United States Patent
Akensov et al.

(10) Patent No.: US 9,206,124 B2
(45) Date of Patent: Dec. 8, 2015

(54) TREATMENT OF DRUG-RESISTANT CANCER WITH 2-ARYL-2-(3-INDOLYL) ACETOHYDROXAMATES

(71) Applicant: New Mexico Technical Research Foundation, Socorro, NM (US)

(72) Inventors: Alexander V. Akensov, Stavropol (RU); Snezna Rogelj, Socorro, NM (US); Liliya Frolova, Socorro, NM (US); Alexander Kornienko, San Marcos, TX (US); Gabriel Avilucea, Socorro, NM (US)

(73) Assignee: New Mexico Technical Research Foundation, Socorro, NM (US)

( * ) Notice: Subject to any disclaimer, the term of this patent is extended or adjusted under 35 U.S.C. 154(b) by 0 days.

(21) Appl. No.: 14/516,543

(22) Filed: Oct. 16, 2014

(65) Prior Publication Data

US 2015/0105439 A1  Apr. 16, 2015

Related U.S. Application Data

(60) Provisional application No. 61/891,746, filed on Oct. 16, 2013.

(51) Int. Cl.
*C07D 209/20* (2006.01)

(52) U.S. Cl.
CPC .................................. *C07D 209/20* (2013.01)

(58) Field of Classification Search
CPC ............................ A61K 31/404; C07D 209/20
See application file for complete search history.

(56) References Cited

PUBLICATIONS

Aksenov et al 'Metal-free transannulation reaction of indoles with nitrostyrenes: a simple practical synthesis of 3 substituted 2 quinolones' Chemical Communications, vol. 49, p. 9305-9307, 2013.*

* cited by examiner

*Primary Examiner* — Wu-Cheng Winston Shen
*Assistant Examiner* — Christopher R Stone
(74) *Attorney, Agent, or Firm* — Jennifer S. Stachniak

(57) ABSTRACT

A pharmaceutical composition, a method of producing same, and a method of providing cancer therapy therein comprising a pharmaceutically acceptable excipient or carrier and a compound Formula 3 as follows:

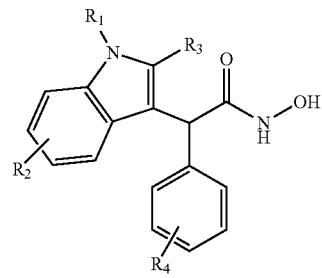

or a pharmaceutically acceptable salt or prodrug thereof, wherein:

$R_1$, $R_2$, $R_3$ and $R_4$ are optionally substituted and are hydrogen, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, acyloxyalkyl, hydroxyl, alkoxy, acetoxy, amino, alkylamino, acetamido.

4 Claims, 5 Drawing Sheets

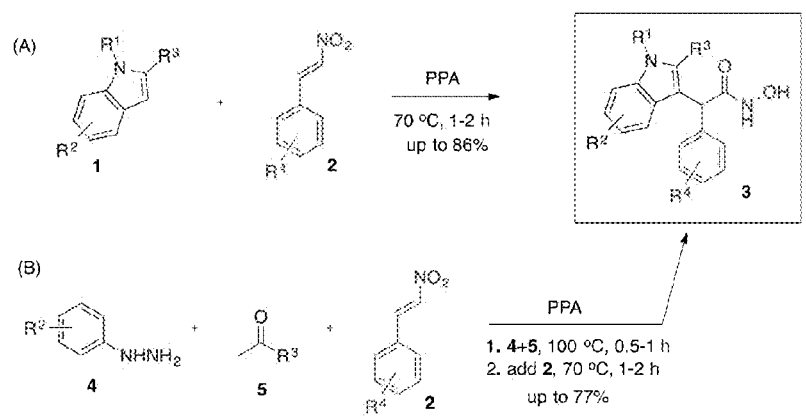
Figure 1. Two synthetic approaches toward 2-aryl-2-(3-indolyl)acetohydroxamates 3

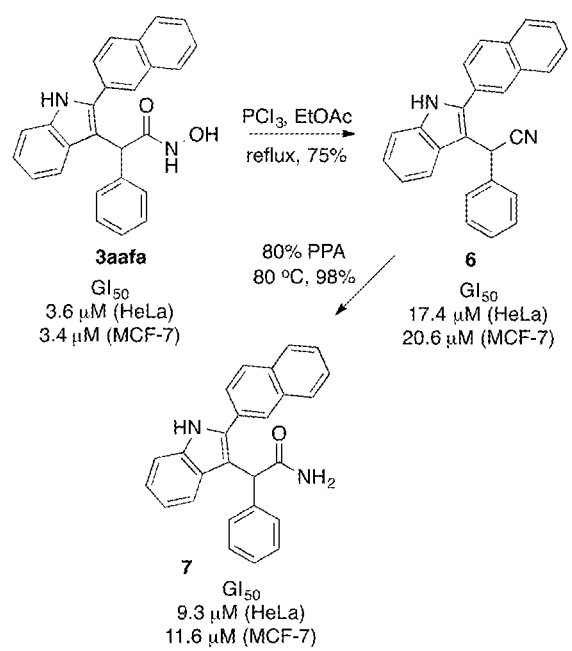
Figure 2. Synthesis of non-hydroxamate analogues of 3

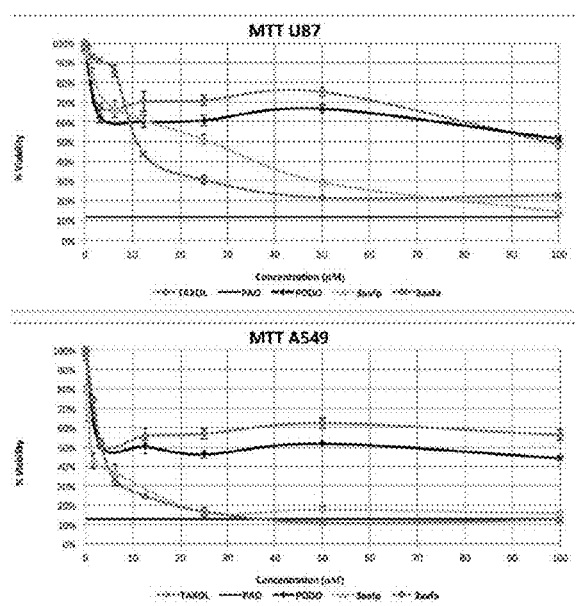
Figure 3. Activity of 3aafp and 3aafa against cell populations resistant to proapoptotic agents.

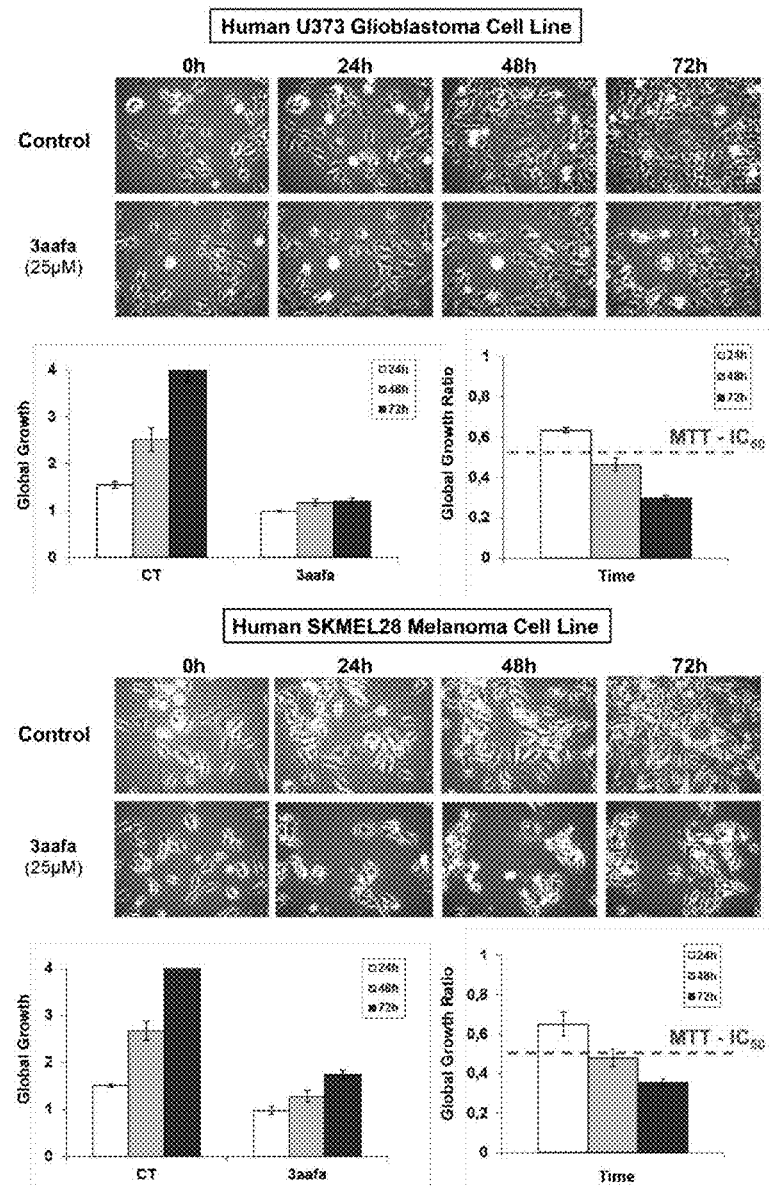
Figure 4. Cellular imaging of 3aafa against SKMEL-28 melanoma and U373 glioblastoma cells illustrating the cytostatic antiproliferative mechanism.

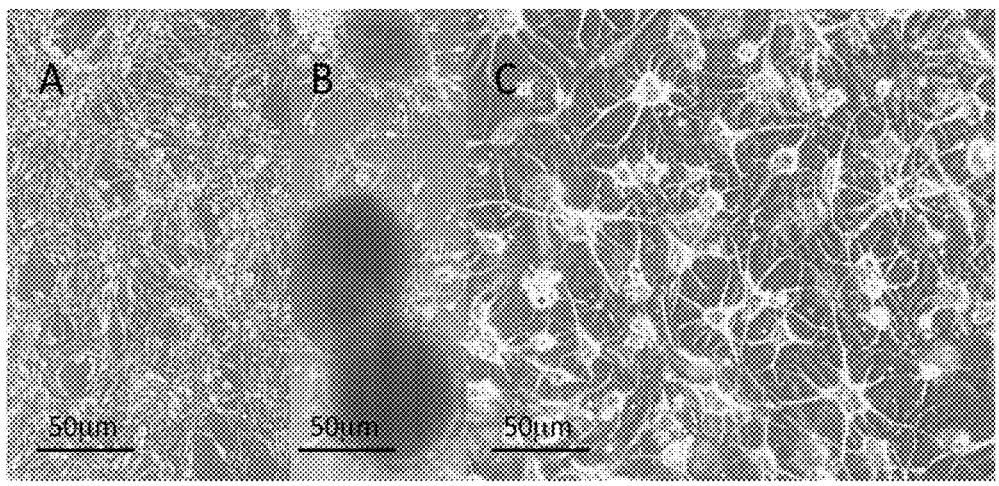
Figure 5. Redifferentiation of growth-inhibited malignant U87 cells to an astrocytic phenotype. (A) Three day old glioblastoma cancer cells. (B) Untreated, these grow into mini-tumors during the following three days. (C) After a 33-day treatment with 7 µM 3aafa.

TREATMENT OF DRUG-RESISTANT CANCER WITH 2-ARYL-2-(3-INDOLYL) ACETOHYDROXAMATES

The present invention relates to the provisional application titled "Activity of 2-(3-indolyl) acetohydroxamates for the Treatment of Drug-Resistant Cancer Cells", filed on Oct. 16, 2013 with the Application No. 61/891,746.

BACKGROUND OF THE INVENTION

Many types of tumors, including glioma, melanoma, non-small cell lung, esophageal, head and neck cancer, among others, are intrinsically resistant to apoptosis induction and poorly responsive to current therapies with proapoptotic agents. In addition, tumors often develop multi-drug resistance based on the cellular efflux of chemotherapeutic agents. Thus, novel anticancer agents capable of overcoming these intrinsic or developed tumor resistance mechanisms are urgently needed. The present application covers a series of 2-aryl-2-(3-indolyl)acetohydroxamic acids, which are active against apoptosis- and multidrug-resistant cancer cells as well as glioblastoma stem-like cell cultures derived from patients. Thus, the described compounds serve as a novel chemical scaffold for the development of potentially highly effective clinical cancer drugs.

Apoptosis-resistant cancers represent a major challenge in the clinic as most of the currently available chemotherapeutic agents work through the induction of apoptosis and, therefore, provide limited therapeutic benefits for the patients affected by these malignancies. Cancers with such intrinsic resistance to proapoptotic stimuli include the tumors of the lung, liver, stomach, esophagus, pancreas as well as melanomas and gliomas. For example, patients afflicted by a type of gliomas, known as glioblastoma multiforme, have a median survival expectancy of less than 14 months when treated with a standard protocol of surgical resection, radiotherapy and chemotherapy with temozolomide, carmustine or cisplatin. Because glioma cells display resistance to apoptosis, they respond poorly to such conventional chemotherapy with proapoptotic agents.

Resistance to apoptosis is also an intrinsic property of tumor metastases. Successful treatment of metastases remains an important clinical challenge as 90% of cancer patients die from metastastic cancer spread. By acquiring resistance to anoikis, a cell death process resulting from the loss of contact with extracellular matrix or neighboring cells, metastatic cells display poor sensitivity to apoptosis induction and are thus poorly responsive to conventional proapoptotic chemotherapeutic agents. One solution to apoptosis resistance entails the complementation of cytotoxic therapeutic regimens with cytostatic agents, and thus a search for novel cytostatic anticancer drugs that can overcome cancer cell resistance to apoptosis is an important pursuit.

Often, tumors are initially susceptible to cancer agents and patients respond to chemotherapy but eventually experience a relapse in spite of the continuing treatment. In such instances of acquired resistance tumors generally become refractory to a broad spectrum of structurally and mechanistically diverse antitumor agents and this phenomenon is referred to as multidrug resistance (MDR). MDR usually results from upregulation of certain protein pumps, such as P-glycoprotein (P-gp) in cancer cells, causing a decreased intracellular drug concentration. MDR is a major factor that contributes to the failure of chemotherapy, for example with such widely used anticancer drugs as the *vinca* alkaloids or the taxanes.

SUMMARY OF THE INVENTION

Our recent studies of a reaction of indole derivatives with β-nitrostyrenes in polyphosphoric acid (PPA) led to the discovery of an efficient synthesis of 2-aryl-2-(3-indolyl)acetohydroxamates. Although 2,2-diarylacetohydroxamates had been previously synthesized and studied for biological activities, compounds in which one of the two aromatic rings is an indole moiety had not been reported in the literature. Thus, 2-aryl-2-(3-indolyl)acetohydroxamate was revealed to be a new chemotype, prompting our thorough investigation of biological properties of compounds incorporating this structural feature. These studies led to the discovery of significant activity associated with a number of synthesized compounds against cancer cell lines displaying resistance to various types of proapoptotic stimuli as well as glioblastoma neurosphere stem-like cell cultures derived from patients. It was also found that the active analogues exhibited their antiproliferative activity through a cytostatic non-apoptotic mechanism of action and maintained their potency against multi-drug resistant cells, which are poorly responsive to important clinical cancer drugs taxol and vinblastine.

BRIEF DESCRIPTION OF THE DRAWINGS

FIG. 1 shows two synthetic approaches toward 2-aryl-2-(3-indolyl)acetohydroxamates 3.

FIG. 2 shows synthesis of non-hydroxamate analogues of 3.

FIG. 3 shows activity of 3aafp and 3aafa against cell populations resistant to proapoptotic agents.

FIG. 4 shows cellular imaging of 3aafa against SKMEL-28 melanoma and U373 glioblastoma cells illustrating the cytostatic antiproliferative mechanism.

FIG. 5 shows redifferentiation of growth-inhibited malignant U87 cells to an astrocytic phenotype. (A) Three day old glioblastoma cancer cells. (B) Untreated, these grow into mini-tumors during the following three days. (C) After a 33-day treatment with 7 μM 3aafa.

Some of the abbreviation used in the following include: ATCC, American Type Culture Collection; DAPI, 4',6-diamidino-2-phenylindole; DMEM, Dulbecco's modified Eagle's medium; DMF, dimethylformamide; DMSO, dimethyl sulfoxide; DSMZ, Deutsche Sammlung von Mikroorganismen and Zellkulturen; ECACC, European Collection of Cell Culture; FBS, fetal bovine serum; FITC, fluorescein isothiocyanate; GGR, global growth ratio; HRMS, high resolution mass spectrometry; MDR, multidrug resistance; MTT, 3-(4, 5-dimethylthiazol-2-yl)-2,5-diphenyltetrazolium bromide; NSCLC, non-small-cell-lung cancer; PAO, phenyl arsine oxide; P-gp, P-glycoprotein; SAR, structure-activity relationship; PPA, polyphosphoric acid; TLC, thin layer chromatography; SD, standard deviation.

Compounds of the application include prodrugs. In general, such prodrugs will be functional derivatives of a compound of the application, which are readily convertible in vivo into the compound from which it is notionally derived. Prodrugs of the compounds of the application may be derivatives of hydroxamic acid, which are masked with groups which can be converted to hydroxyl in vivo, such as esters, acid-labile ethers, among others. Conventional procedures for the selection and preparation of suitable prodrugs are described, for example, in "Design of Prodrugs" ed. H. Bundgaard, Elsevier, 1985.

The term "cancer" as used herein refers to a class of diseases or disorders characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system. Examples of cancer may be treated using the compounds of the application include but are not limited to glioblastoma, melanoma, non-small cell lung cancer, head-and-neck cancer, prostate cancer, colon cancer, breast cancer, bladder cancer, ovarian cancer, cervical cancer, endometrial cancer, renal cancer and pancreatic cancer.

The compounds of the application are suitably formulated into pharmaceutical compositions for administration to human subjects in a biologically compatible form suitable for administration in vivo. Accordingly, the present application further includes a pharmaceutical composition comprising one or more compounds of Formula I, as defined above, and/or pharmaceutically acceptable salts, solvates and/or prodrugs thereof, and a pharmaceutically acceptable carrier and/or diluent.

The pharmaceutical compositions containing the compounds of the application can be prepared by known methods for the preparation of pharmaceutically acceptable compositions, which can be administered to subjects, such that an effective quantity of the active substance is combined in a mixture with a pharmaceutically acceptable vehicle. Suitable vehicles are described, for example, in Remington's Pharmaceutical Sciences (2000-20$^{th}$ edition) and in the United States Pharmacopeia: The National Formulary (USP 24NF19) published in 1999. On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of the application are used in the form of the free hydroxamates, in the form of prodrugs, salts and/or solvates. All forms, including mixtures thereof, are within the scope of the application.

Chemistry

2-Aryl-2-(3-indolyl)acetohydroxamates (3, FIG. 1) were identified to be intermediates in our recently discovered transannulation of indoles to 2-quinolones carried out by reacting 2-substituted indoles with β-nitrostyrenes in PPA at 100° C. It was found that if the reaction temperature was kept at 70° C., compounds 3 could be isolated as the main reaction products (FIG. 1A, Tables 1 and 2). The reaction scope was found to allow for the introduction of a variety of substituents $R^1$, $R^2$, $R^3$ and $R^4$ into the 2-aryl-2-(3-indolyl)acetohydroxamate scaffold 3. In addition, the recognition of limited access to a number of specific substituted indoles that would be required for systematic structure-activity relationship (SAR) analyses prompted the development of an alternative route based on an in situ Fisher indole synthesis utilizing arylhydrazines 4 and ketones 5 (FIG. 1B). In this multicomponent variation, compounds 4 and 5 are reacted at 100° C. to allow for the indole formation and then the reaction temperature is lowered to 70° C. prior to the introduction of β-nitrostyrenes 2. Thus, the availability of two complementary approaches to compounds 3 permits the synthesis of analogues with the desired identity and positioning of substituents $R^1$, $R^2$, $R^3$ and $R^4$ on the 2-aryl-2-(3-indolyl)acetohydroxamate scaffold facilitating the development of these compounds as medicinal agents. Since the synthesized compounds have four diversification points, a four-dimensional tagging system is employed for labeling the products. Thus, the reaction of hydrazine 4aa with ketone 5f produces indole 1aaf, which in the subsequent reaction with nitrostyrene 2n affords hydroxamic acid 3aafn (see Experimental Section for these compounds).

Pharmacology (a) SAR Analyses

The evaluation of an initially synthesized series of compounds 3 for a variety of activities led to the identification of double-digit micromolar antiproliferative potencies associated with the parent acetohydroxamate 3aaaa (Table 1). This finding led to an exploration of the SAR analyses by synthesizing the first generation compounds 3 containing diverse substituents at different positions in the 2-aryl-2-(3-indolyl)acetohydroxamate skeleton and testing this series for in vitro growth inhibition using the MTT colorimetric assay against two cell lines, human HeLa cervical and MCF-7 breast adenocarcinomas (Table 1). It emerged from these experiments that the substitution on the benzene ring of the indole moiety ($R^2 \neq H$) was not tolerated (e.g., 3abfa and 3acfa), whereas the nitrogen could be derivatized ($R^1 \neq H$) with only a small activity drop (e.g., 3bafa vs 3aafa). The key SAR finding resulted from the variations of the C2-position of the indole moiety ($R^3 \neq Ph$ as in 3aaba, 3aaca, 3aada, 3aaea and 3aafa) and identification of single-digit micromolar potencies associated with compounds containing the β-naphthyl substituent at this position (as in 3aafa).

TABLE 1

Structures, synthetic yields (methods A or B) and antiproliferative activities of the first generation compounds 3

| # logP | structure | % yield (method) | cell viability$^a$ GI$_{50}$, µM HeLa | MCF7 |
|---|---|---|---|---|
| 3aaaa 4.1 ± 0.1 | 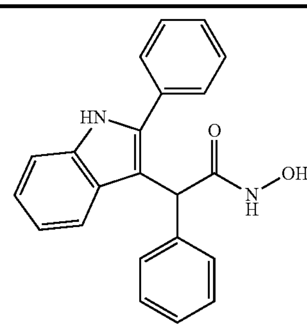 | 82 (A) 76 (B) | 23.0 ± 2.6 | 31.0 ± 0.6 |

TABLE 1-continued

Structures, synthetic yields (methods A or B) and antiproliferative activities of the first generation compounds 3

| # | | | cell viability$^a$ | |
| | | % yield | GI$_{50}$, μM | |
| logP | structure | (method) | HeLa | MCF7 |
| --- | --- | --- | --- | --- |
| 3aaab 4.1 ± 0.1 | [2-phenyl-1H-indol-3-yl, N-hydroxy, 4-nitrophenyl acetamide] | 73 (A) 68 (B) | >50 | >50 |
| 3aaba 4.1 ± 0.1 | [2-(2-nitrophenyl)-1H-indol-3-yl, N-hydroxy, phenyl acetamide] | 68 (A) 61 (B) | >50 | >50 |
| 3aaca 4.1 ± 0.1 | [2-(4-methoxyphenyl)-1H-indol-3-yl, N-hydroxy, phenyl acetamide] | 43 (A) 35 (B) | >50 | >50 |
| 3aada 2.7 ± 0.1 | [2-methyl-1H-indol-3-yl, N-hydroxy, phenyl acetamide] | 46 (A) 27 (B) | >50 | >50 |

TABLE 1-continued

Structures, synthetic yields (methods A or B) and antiproliferative activities of the first generation compounds 3

| # logP | structure | % yield (method) | cell viability[a] GI$_{50}$, μM | |
|---|---|---|---|---|
| | | | HeLa | MCF7 |
| 3aaea 5.2 ± 0.0 | 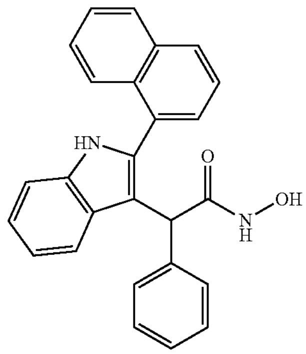 [SMILES: O=C(NO)C(c1ccccc1)c1c(-c2cccc3ccccc23)[nH]c2ccccc12] | 76 (A) 70 (B) | 25.7 ± 1.6 | 32.0 ± 0.9 |
| 3aafa 4.1 ± 0.1 | 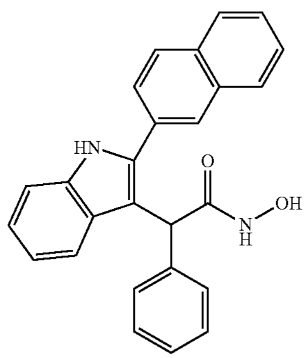 [SMILES: O=C(NO)C(c1ccccc1)c1c(-c2ccc3ccccc3c2)[nH]c2ccccc12] | 85 (A) 73 (B) | 3.6 ± 0.5 | 3.4 ± 0.3 |
| 3abfa 5.7 ± 0.1 | 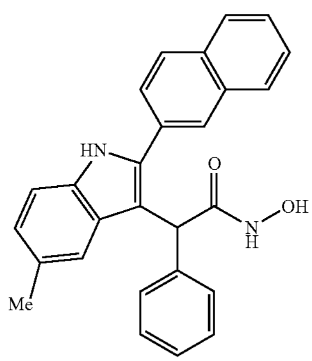 [SMILES: Cc1ccc2[nH]c(-c3ccc4ccccc4c3)c(C(C(=O)NO)c3ccccc3)c2c1] | 79 (A) 73 (B) | >50 | >50 |
| 3acfa 5.2 ± 0.1 | 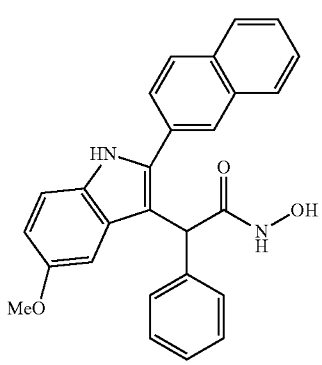 [SMILES: COc1ccc2[nH]c(-c3ccc4ccccc4c3)c(C(C(=O)NO)c3ccccc3)c2c1] | 28 (B) | >50 | >50 |

TABLE 1-continued

Structures, synthetic yields (methods A or B) and antiproliferative activities of the first generation compounds 3

| # logP | structure | % yield (method) | cell viability[a] $GI_{50}$, µM HeLa | MCF7 |
|---|---|---|---|---|
| 3bafc 5.5 ± 0.1 | 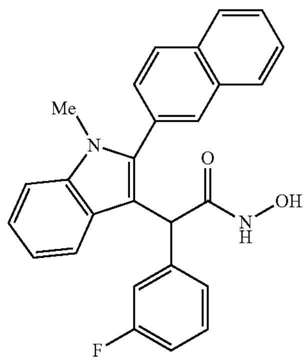 [SMILES: Cn1c(-c2ccc3ccccc3c2)c(C(C(=O)NO)c2cccc(F)c2)c2ccccc21] | 54 (A) | 36.8 ± 0.4 | 25.7 ± 1.4 |
| 3bafa 5.4 ± 0.0 | 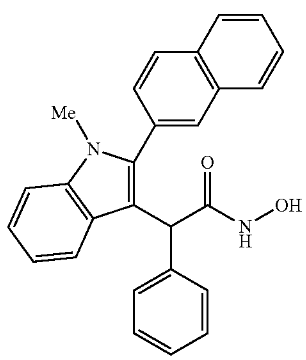 [SMILES: Cn1c(-c2ccc3ccccc3c2)c(C(C(=O)NO)c2ccccc2)c2ccccc21] | 75 (A) | 19.7 ± 1.7 | 10.0 ± 0.3 |
| 3bafd 6.2 ± 0.0 | 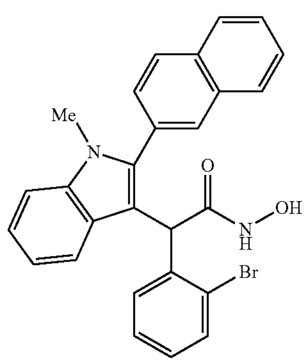 [SMILES: Cn1c(-c2ccc3ccccc3c2)c(C(C(=O)NO)c2ccccc2Br)c2ccccc21] | 36 (A) | 24.0 ± 0.2 | 11.2 ± 0.9 |

[a]Concentration required to reduce the viability of cells by 50% after a 48 h treatment with the indicated compounds relative to a DMSO control ± SD from two independent experiments, each performed in 4 replicates, as determined by the MTT assay.

Based on the initial SAR in Table 1, the second generation compounds 3 were synthesized and they all contained an $R^2$=β-naphthyl, while $R^1$ and $R^4$ remained variable. These experiments led to the identification of a number of compounds possessing single-digit micromolar (e.g., 3aafe, 3aafk, 3aafm, 3aafn, 3aafo and 3aafp) or even submicromolar (e.g., 3aafe and 3aafp) activities, all containing meta and/or para-positioned $R^4$. The addition of an $R^1$=alkyl (e.g., 3cafa, 3dafa, 3cafe and 3eafa) did not appear to be detrimental, with $GI_{50}$ values still in the single-digit micromolar region. To confirm that the activities were not a function of compound's lipophilicities, log P values were calculated for each analogue using three different methods, all giving similar results (Tables 1 and 2). The significant activity was indeed present among both less lipophilic analogues (e.g., 3aafc with log P=4.1) and those with higher lipophilicity (e.g., 3cafe with log P=8.4), thus ruling out such a possibility.

TABLE 2

Structures, synthetic yields (methods A or B) and antiproliferative activities of second generation compounds 3

| # logP | structure | % yield (method) | cell viability$^a$ GI$_{50}$, μM | |
|---|---|---|---|---|
| | | | HeLa | MCF7 |
| 3aafe 6.7 ± 0.2 | 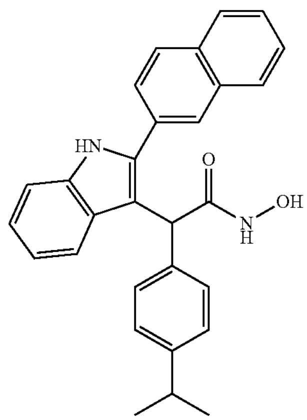 [SMILES: CC(C)c1ccc(C(C(=O)NO)c2c(-c3ccc4ccccc4c3)[nH]c3ccccc23)cc1] | 73 (A) 61 (B) | 0.68 ± 0.04 | 1.4 ± 0.1 |
| 3aaff 4.9 ± 0.0 | 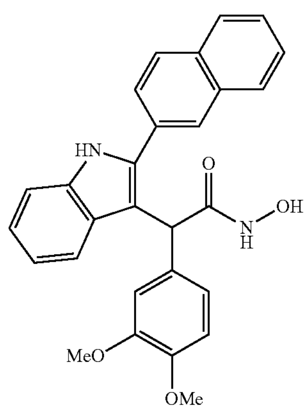 [SMILES: COc1ccc(C(C(=O)NO)c2c(-c3ccc4ccccc4c3)[nH]c3ccccc23)cc1OC] | 60 (A) 56 (B) | 26.9 ± 0.3 | 2.4 ± 0.1 |
| 3aafg 5.4 ± 0.1 | 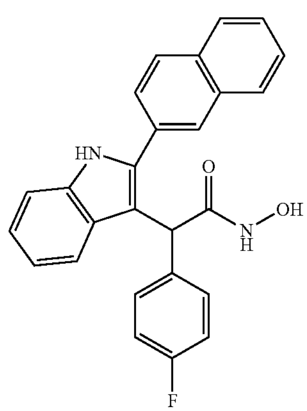 [SMILES: O=C(NO)C(c1ccc(F)cc1)c1c(-c2ccc3ccccc3c2)[nH]c2ccccc12] | 76 (A) 64 (B) | 18.2 ± 0.9 | 6.3 ± 1.1 |

TABLE 2-continued
Structures, synthetic yields (methods A or B) and antiproliferative activities of second generation compounds 3
| # logP | structure | % yield (method) | cell viability[a] GI$_{50}$, μM | |
|---|---|---|---|---|
| | | | HeLa | MCF7 |
| 3aafh 5.9 ± 0.1 | 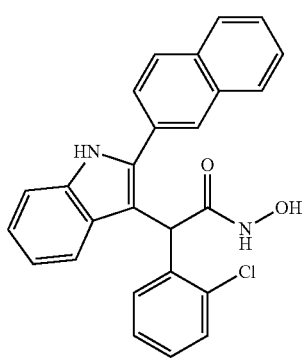 [SMILES: O=C(NO)C(c1ccccc1Cl)c1c(-c2ccc3ccccc3c2)[nH]c2ccccc12] | 84 (A) 72 (B) | 31.0 ± 0.2 | 4.9 ± 0.1 |
| 3aafi 6.5 ± 0.1 | 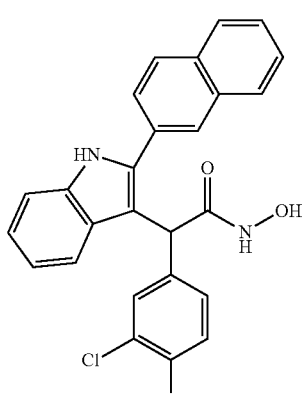 | 45 (A) 43 (B) | 31.7 ± 1.7 | 12.2 ± 1.0 |
| 3aafc 4.1 ± 0.1 | 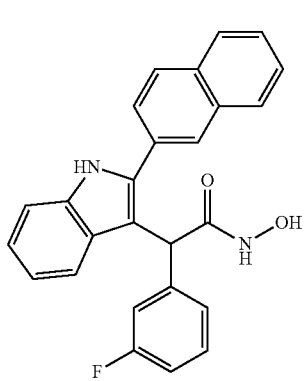 [SMILES: O=C(NO)C(c1cccc(F)c1)c1c(-c2ccc3ccccc3c2)[nH]c2ccccc12] | 75 (A) 64 (B) | 32.9 ± 1.1 | 20.4 ± 0.1 |

TABLE 2-continued
Structures, synthetic yields (methods A or B) and antiproliferative activities of second generation compounds 3
| # logP | structure | % yield (method) | cell viability$^a$ GI$_{50}$, μM | |
|---|---|---|---|---|
| | | | HeLa | MCF7 |
| 3aafj 6.3 ± 0.1 | 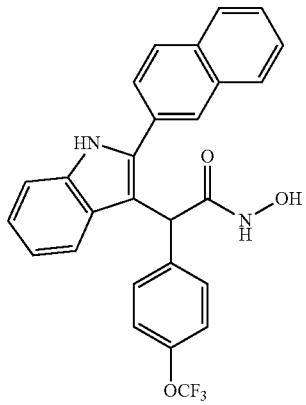 [SMILES: O=C(NO)C(c1ccc(OC(F)(F)F)cc1)c1c(-c2ccc3ccccc3c2)[nH]c2ccccc12] | 56 (A) 52 (B) | 27.4 ± 0.2 | 10.2 ± 0.1 |
| 3aafk 6.1 ± 0.2 | 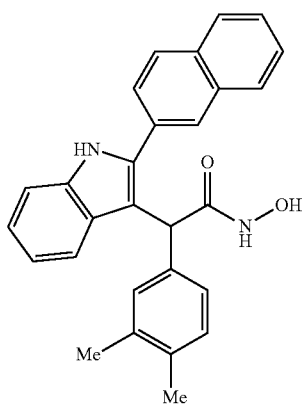 [SMILES: Cc1ccc(C(C(=O)NO)c2c(-c3ccc4ccccc4c3)[nH]c3ccccc23)cc1C] | 70 (A) 59 (B) | 2.7 ± 0.1 | 2.5 ± 0.1 |
| 3aafd 6.2 ± 0.0 | 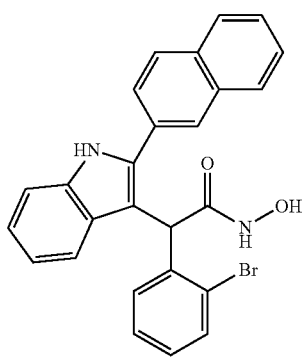 [SMILES: O=C(NO)C(c1ccccc1Br)c1c(-c2ccc3ccccc3c2)[nH]c2ccccc12] | 57 (A) 55 (B) | 13.0 ± 0.4 | 2.7 ± 0.0 |

TABLE 2-continued

Structures, synthetic yields (methods A or B) and antiproliferative activities of second generation compounds 3

| # logP | structure | % yield (method) | cell viability$^a$ GI$_{50}$, μM | |
|---|---|---|---|---|
| | | | HeLa | MCF7 |
| 3aafl 5.6 ± 0.2 | (2-naphthyl-indole with CH(4-OEt-phenyl)C(O)NHOH) | 81 (A) 72 (B) | 17.3 ± 0.2 | 8.5 ± 0.3 |
| 3aafm 5.7 ± 0.1 | (2-naphthyl-indole with CH(4-Me-phenyl)C(O)NHOH) | 80 (A) 72 (B) | 6.3 ± 1.3 | 4.9 ± 0.2 |
| 3aafn 5.7 ± 0.1 | (2-naphthyl-indole with CH(3-Me-phenyl)C(O)NHOH) | 76 (A) 69 (B) | 6.9 ± 0.4 | 7.4 ± 0.6 |

TABLE 2-continued

Structures, synthetic yields (methods A or B) and antiproliferative activities of second generation compounds 3

| # logP | structure | % yield (method) | cell viability[a] GI$_{50}$, μM | |
|---|---|---|---|---|
| | | | HeLa | MCF7 |
| 3aafo 6.0 ± 0.1 | (2-naphthyl-indole with CH(4-NEt$_2$-C$_6$H$_4$)CONHOH) | 53 (A) 50 (B) | 4.1 ± 0.2 | 7.9 ± 0.7 |
| 3aafp 5.3 ± 0.1 | (2-naphthyl-indole with CH(4-NMe$_2$-C$_6$H$_4$)CONHOH) | 45 (A) 43 (B) | 0.60 ± 0.02 | 1.1 ± 0.0 |
| 3cafa 6.8 ± 0.1 | (N-butyl-2-naphthyl-indole with CH(Ph)CONHOH) | 83 (A) | 5.6 ± 0.3 | 7.8 ± 0.6 |

TABLE 2-continued

Structures, synthetic yields (methods A or B) and antiproliferative activities of second generation compounds 3

| # logP | structure | % yield (method) | cell viability[a] $GI_{50}$, μM | |
|---|---|---|---|---|
| | | | HeLa | MCF7 |
| 3dafa 6.7 ± 0.1 | 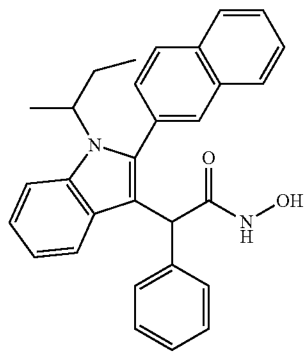 [SMILES: CCC(C)n1c(-c2ccc3ccccc3c2)c(C(C(=O)NO)c2ccccc2)c2ccccc21] | 80 (A) | 9.8 ± 0.8 | 9.3 ± 0.3 |
| 3cafe 8.4 ± 0.1 | 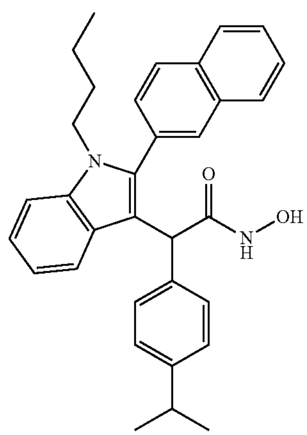 [SMILES: CCCCn1c(-c2ccc3ccccc3c2)c(C(C(=O)NO)c2ccc(C(C)C)cc2)c2ccccc21] | 68 (A) | 6.6 ± 0.5 | 7.7 ± 0.4 |
| 3eafa 7.0 ± 0.1 | 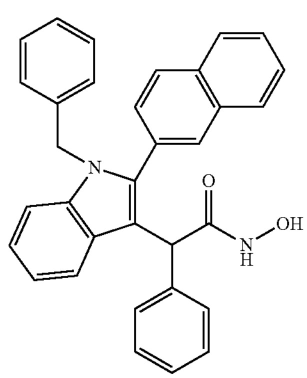 [SMILES: O=C(NO)C(c1ccccc1)c1c(-c2ccc3ccccc3c2)n(Cc2ccccc2)c2ccccc12] | 75 (A) | 5.4 ± 0.3 | 5.5 ± 0.2 |

[a]Concentration required to reduce the viability of cells by 50% after a 48 h treatment with the indicated compounds relative to a DMSO control ± SD from two independent experiments, each performed in 4 replicates, as determined by the MTT assay.

Finally, to assess the importance of the hydroxamic acid moiety, 3aafa was converted to nitrile 6 by treating the former with $PCl_3$ and further to amide 7 by partial hydration of 6 in 80% PPA (FIG. 2). The evaluation of nitrile 6 and amide 7 for antiproliferative activity revealed a 6- and 3-fold lower potencies associated with these compounds as compared with hydroxamate 3aafa, thus underscoring the importance of the hydroxamic acid moiety but not its criticality.

(b) Activity Against Cells Exhibiting Various Types of Resistance to Proapoptotic Stimuli As part of the ongoing efforts aimed at identification of compounds active against cancer cells displaying resistance to proapoptotic agents, the selected 2-aryl-2-(3-indolyl)-acetohydroxamates were evaluated for in vitro growth inhibition against a panel of additional cancer cell lines including those resistant to various proapoptotic stimuli, such as human T98G and U87 glioblastoma and human A549 non-small-cell-lung cancer (NSCLC), as well as an apoptosis-sensitive tumor model, such as human Hs683 anaplastic oligodendroglioma, used as a reference. The obtained $GI_{50}$ values associated with potent hydroxamates are shown in Table 3. The data reveal that for the most part these compounds retain the single-digit antiproliferatve $GI_{50}$ values in this challenging cancer cell panel. Further analysis of the results from Tables 2 and 3 combined shows that the hydroxamates do not discriminate between the cancer cell lines based on the apoptosis sensitivity criterion and display comparable potencies in both cell types, indicating that apoptosis induction is not the primary mechanism responsible for antiproliferative activity in this series of compounds.

TABLE 3

Antiproliferative properties of potent hydroxamates against cancer cell lines displaying apoptosis resistance and representing cancers with dismal prognoses

| | $GI_{50}$ in vitro values (μM)[a] | | | |
|---|---|---|---|---|
| | glioma | | | lung carcinoma |
| compound | Hs683 | U87 | T98G | A549 |
| 3aafa | 8.9 ± 0.4 | 9.5 ± 0.3 | 36.4 ± 1.9 | 2.8 ± 0.4 |
| 3aafe | 6.1 ± 1.0 | 5.0 ± 0.5 | 8.8 ± 0.5 | 3.3 ± 0.6 |
| 3aafk | 4.7 ± 1.0 | 6.7 ± 1.5 | 7.5 ± 0.8 | 2.9 ± 0.6 |
| 3cafa | 10.8 ± 0.5 | 6.7 ± 0.3 | 12.3 ± 0.8 | 5.7 ± 0.5 |
| 3eafa | 11.2 ± 0.9 | 9.1 ± 0.3 | 10.6 ± 0.4 | 5.8 ± 0.8 |
| 3aafp | 5.1 ± 0.5 | 21.3 ± 1.6 | 1.9 ± 0.2 | 1.5 ± 0.3 |

[a]Concentration required to reduce the viability of cells by 50% after a 48 h treatment with the indicated compounds relative to a DMSO control ± SD from two independent experiments, each performed in 4 replicates, as determined by the MTT assay.

Our previous experience of working with cells resistant to various proapoptotic stimuli shows that generally a certain population of cells becomes rapidly eliminated with proapoptotic agents used at low concentrations, leading to low $GI_{50}$ values. However, these high potencies can be somewhat misleading as there often remains a significant portion of cells that resists the effects of the proapoptotic agents even at concentrations 100- or 1000-fold of their $GI_{50}$s. It was thus instructive to compare the hydroxamates with common proapoptotic agents for their ability to affect such resistant populations. Indeed, as can be seen in FIG. 3, hydroxamates 3aafa and 3aafp have potent growth inhibitory properties against most of the cells in U87 and A549 cultures and, with increasing concentration, rapidly reach antiproliferative levels of a non-discriminate cytotoxic agent phenyl arsine oxide (PAO). In contrast, common proapoptotic agents taxol and podophyllotoxin have no effect on proliferation of ca. 50% of cells in these cultures at concentrations up to 100 μM.

(c) Quantitative Videomicroscopy

To obtain insight into the effectiveness of 2-aryl-2-(3-indolyl)acetohydroxamates against apoptosis-resistant cancers, computer-assisted phase-contrast microscopy (quantitative videomicroscopy) was employed to observe the phenotypic morphological changes in cancer cells as they are treated with these compounds. FIG. 4 shows that acetohydroxamate 3aafa inhibits cancer cell proliferation without inducing cell death when assayed at concentrations slightly exceeding the $GI_{50}$ values (25 μM) in SKMEL-28 melanoma and U373 glioblastoma cells, both exhibiting resistance to various proapoptotic stimuli. Based on the phase contrast pictures obtained by means of quantitative videomicroscopy, a global growth ratio (GGR) was calculated, which corresponds to the ratio of the mean number of cells present in a given image captured in the experiment (in this case after 24, 48 and 72 h) to the number of cells present in the first image (at 0 h). The ratio obtained in the 3aafa-treated experiment was then divided by the ratio obtained in the control. The GGR value of ca. 0.3 in both of these two cell lines indicates that 30% of cells grew in the 3aafa-treated experiment as compared to the control over a 72 h observation period. Thus, the GGR calculations are consistent with the MTT colorimetric data and indicate that it is the cytostatic properties associated with the hydroxamates that are responsible for their antiproliferative effects against apoptosis-resistant cancer cells, at least at relevant concentrations (slightly above the $GI_{50}$ values).

(d) Redifferentiation of U87 Cells to an Astrocytic Phenotype

To elucidate the fate of the cells whose growth has been arrested with the hydroxamates, the phenotypic morphological changes of U87 glioma cells were observed for a period of several weeks after the treatment with hydroxamate 3aafa at the $GI_{50}$ concentration. Interestingly, while untreated cells proliferated rapidly and quickly formed spheroids (FIG. 5B), the treated cells ceased to replicate and appeared to undergo redifferentiation to a non-malignant state resembling an astrocytic phenotype (FIG. 5C). Although such redifferentiation processes are known, there are only a few small molecule agents reported to induce these epigenetic transformations. The literature reports indicate that these redifferentiated cells possess significantly reduced tumorigenicity in vivo and, thus, new chemical entities capable of triggering such phenotypic changes hold a promising but completely unexplored potential as anticancer agents.

(e) Activity Against MDR Cells and Glioblastoma Neurosphere Stem Like Cell Cultures Derived from Patients Compared with the intrinsic drug resistance, as described above for such cancers as glioblastoma and melanoma, a large variety of tumors can also develop resistance to anticancer drugs resulting in MDR as explained previously. To assess whether the hydroxamates can overcome this resistance mechanism, selected hydroxamates were tested against MDR cells (Table 4). The MDR uterine sarcoma cell line MES-SA/Dx5 was utilized for this experiment. This cell line was established from the parent uterine sarcoma MES-SA, grown in the presence of increasing concentrations of doxorubicin and known to be resistant to a number of P-gp substrates. Both taxol and vinblastine displayed more than a thousand fold drop in potency when tested for antiproliferative activity against the MDR cell line as compared with the parent line (Table 4). In contrast, there was only a small variation in the sensitivities of the two cell lines towards the hydroxamates indicating their potential to overcome clinical multi-drug resistance.

Given the ability of the hydroxamates to overcome drug resistance a few select compounds were further evaluated against glioma cells grown in neurosphere conditions, which are known to promote the growth of stem-like cells from human glioma tissue. Indeed, the neurospheres show the ability of self-renewal by regrowing in culture from individual cells, and can differentiate into multiple neural lineages and recapitulate human gliomas on both histological and genetic levels more faithfully than serum cultured glioma cell lines when injected into the brains of mice. Because, neurosphere cells are generally resistant to radiation and chemotherapy, the micromolar to submicromolar activity of the hydroxamates against the glioma neurosphere cell cultures is noteworthy (Table 4). The glioma culture 031810 used is derived from a patient with glioblastoma who progressed on temozolomide due to high $O^6$-methylguanine-DNA-methyltransferase (MGMT) expression and thus shows high resistance to this agent (Table 4). It is worthy of note, that the unmethylated MGMT promoter leading to such temozolomide resistance is found in about half of all GBM patients, who respond poorly to temozolomide chemotherapy. To date, no alternative treatment exists for this group of patients.

TABLE 4

Antiproliferative effect of selected compounds against MDR cells and patient-derived GBM neurosphere cells

| compound | GI$_{50}$ in vitro values (µM) | | |
|---|---|---|---|
| | MES-SA[a] | MES-SA/Dx5[a] | GBM 031810[b] |
| Taxol | 0.007 ± 0.001 | 9.8 ± 0.3 | |
| Vinblastine | 0.006 ± 0.001 | 5.0 ± 1.4 | |
| Temozolomide | | | >1000 |
| 3aafa | 2.0 ± 0.2 | 4.0 ± 1.1 | 0.8 ± 0.6 |
| 3aafp | 0.8 ± 0.1 | 1.6 ± 0.6 | 5.6 ± 0.8 |
| 3aafe | 1.7 ± 0.4 | 4.9 ± 1.9 | 3.4 ± 0.7 |
| 3aafk | 1.8 ± 0.4 | 2.2 ± 0.8 | |
| 3cafa | 5.9 ± 1.7 | 2.7 ± 0.3 | |
| 3eafa | 7.1 ± 0.1 | 8.5 ± 0.9 | |

[a]Concentration required to reduce the viability of cells by 50% after a 48 h treatment with the indicated compounds relative to a DMSO control ± SD from two independent experiments, each performed in 4 replicates, as determined by the MTT assay.
[b]Average IC$_{50}$ ± SD from three IC$_{50}$ determinations.

Conclusion

Drug resistance is one of the main causes for the failure of cancer chemotherapy, affecting patients with a broad variety of tumors. Resistance to chemotherapy can be intrinsic, in which cancers such as glioma, melanoma or NSCLC, among others, fail to respond to the first chemotherapy given. Resistance can also be acquired, in which tumors innately respond to chemotherapy but eventually become refractory to a broad spectrum of structurally and mechanistically diverse antitumor agents. The results presented herein demonstrate the potential of 2-aryl-2-(3-indolyl)acetohydroxamates for the treatment of drug-resistant cancer, regardless of whether the latter harbors intrinsic and acquired resistance mechanisms. The structural scaffold associated with these compounds represents a new chemotype, whose further investigation is warranted by the described findings and should be facilitated by the straightforward synthetic methodologies developed to accommodate systematic SAR studies as well as preparation of specific designed analogues. The ongoing work includes further optimization of compound potency, elucidation of mechanisms responsible for cytostatic and redifferentiation effects as well as experiments involving animal models of drug-resistant human cancer.

EXPERIMENTAL SECTION

General Experimental

Reagents, solvents and catalysts were purchased from commercial sources (Acros Organics and Sigma-Aldrich) and used without purification. All reactions were performed in oven-dried flasks open to the atmosphere and monitored by thin layer chromatography on TLC precoated (250 µm) silica gel 60 F254 glass-backed plates (EMD Chemicals Inc.). Visualization was accomplished with UV light. Filtration was performed using silica gel (32-63 µm, 60 Å pore size). $^1$H and $^{13}$C NMR spectra were recorded on Bruker DRX-400 and Bruker DRX-500 spectrometers. Chemical shifts (δ) are reported in ppm relative to the TMS internal standard. Abbreviations are as follows: s (singlet), d (doublet), t (triplet), q (quartet), m (multiplet). Indoles: 2-phenyl-1H-indole (1aaa), 2-(2-nitrophenyl)-1H-indole (3aab), 2-(4-methoxyphenyl)-1H-indole (3aac), 2-methyl-1H-indole (3aad), 2-(naphthalen-1-yl)-1H-indole (1aae), 2-(naphthalen-2-yl)-1H-indole (1 aaf), 1-methyl-2-(naphthalen-2-yl)-1H-indole (1 baf), and 5-methoxy-2-(naphthalen-2-yl)-1H-indole (1acf) were purchased from commercial sources and used as received. Procedures for preparation of 5-methyl-2-(naphthalen-2-yl)-1H-indole (1abf), 1-butyl-2-(naphthalen-2-yl)-1H-indole (1caf), 1-(sec-butyl)-2-(naphthalen-2-yl)-1H-indole (1daf), 1-benzyl-2-(naphthalen-2-yl)-1H-indole (1eaf) are provided below. Ketones: acetophenone (5a), 0-nitroacetophenone (5b), p-methoxyacetophenone (5c), acetone (5d), 1-acetylnaphalene (5e), and 2-acetylnaphalene (5f) were obtained from commercial sources and used as received. Arylhydrazines: pehylhydrazine (4aa), p-tolylhydrazine (4ab), and p-anisylhydrazine (4ac) were obtained from commercial sources and used as received. Nitroalkenes: (2-nitrovinyl)benzene (2a), 1-nitro-4-(2-nitrovinyl)benzene (2b), 1-fluoro-3-(2-nitrovinyl)benzene (2c), 1-bromo-2-(2-nitrovinyl)benzene (2d), 1,2-dimethoxy-4-(2-nitrovinyl)benzene (2f), 1-chloro-2-(2-nitrovinyl)benzene (2h), 1,2-dichloro-4-(2-nitrovinyl)benzene (2i), 1-(2-nitrovinyl)-4-(trifluoromethoxy)benzene (2j), 1-methyl-4-(2-nitrovinyl)benzene (2m), N,N-dimethyl-4-(2-nitrovinyl)aniline (2p) were acquired from commercial sources and used as received. 1-Isopropyl-4-(2-nitrovinyl)benzene (2e), 1-fluoro-4-(2-nitrovinyl)benzene (2g), 1,2-dimethyl-4-(2-nitrovinyl)benzene (2k), 1-ethoxy-4-(2-nitrovinyl)benzene (2l), 1-methyl-3-(2-nitrovinyl)benzene (2n) were synthesized using a reported procedure,[45] as well as N,N-diethyl-4-(2-nitrovinyl)aniline (2o). Elemental analyses were performed using a CHN-1 analyzer. HRMS analyses were performed on ESI Bruker Maxis. The synthesized compounds were at least 95% pure according to elemental analyses and/or HPLC chromatograms.

Compound 1abf:

A mixture of 4-methylphenylhydrazine (4ab) (1.22 g, 10 mmol) and 2-acetylnaphthalene (5f) (1.70 g, 10 mmol) was vigorously stirred at 100-110° C. in 80% PPA (3-5 g) for 40 min. When the reaction was complete based on TLC analysis the mixture was cooled down to rt, poured into water (50 mL), and neutralized with aqueous ammonia. The formed precipitate was filtered, dried in vacuum, and used without additional purification. Yield 2.44 g (9.5 mmol, 95%); m.p.=212-213° C. (toluene); $^1$H NMR (400 MHz, CDCl$_3$) δ, ppm: 8.43 (br. s, 1H), 8.08 (s, 1H), 7.93-7.86 (m, 4H), 7.56-7.48 (m, 2H), 7.46 (s, 1H), 7.30-7.34 (m, 1H), 7.07 (d, J=8.2 Hz, 1H), 6.9 (s. 1H), 2.49 (s. 3H); $^{13}$C NMR (100 MHz, CDCl$_3$) δ: 133.7, 129.8, 128.9, 128.7, 128.4, 128.1, 127.9, 126.8, 126.7, 126.4, 126.3, 125.4, 124.9, 124.4, 123.9, 120.6, 118.2, 111.0, 21.6; HRMS calc'd for C$_{19}$H$_{16}$N (M+H)$^+$: 258.1277. found 258.1276.

Compound 1aaf:

To a stirred solution of KOH (2.24 g, 40 mmol) in DMSO (20 mL was added 2-(2-naphthyl)indole (1aaf) (2.43 g, 10 mmol), and the mixture was stirred for 45 min. Then, n-butyl bromide (2.7 g, 20 mmol) was added and the stirring was continued for additional 45 min. The mixture was diluted with water (20 mL) and extracted with benzene (3×50 mL). Combined organic layers were washed with water (3×100 mL), dried with CaCl$_2$ and concentrated in vacuum to obtain the titled compound as yellowish oil. Yield 2.60 g (8.7 mmol, 87%); $^1$H NMR (400 MHz, CDCl$_3$) δ, ppm: 7.99-7.92 (m, 4H), 7.77 (d, J=7.8 Hz, 1H), 7.65 (dd, J=8.4, 1.7 Hz, 1H), 7.58-7.55 (m, 2H), 7.45 (d, J=8.2 Hz, 1H), 7.28 (ddd, J=7.4, 7.6, 1.1 Hz, 1H), 7.19 (ddd, J=7.4, 7.4, 0.9 Hz, 1H), 6.65 (s, 1H), 4.25 (t, J=7.5 Hz, 2H), 1.74 (m, 2H), 1.21 (m, 2H), 0.82 (t, J=7.4 Hz, 3H); $^{13}$C NMR (100 MHz, CDCl$_3$) δ: 141.5, 137.7, 133.4, 132.9, 130.9, 128.5, 128.4, 128.3, 128.2, 127.9, 127.4, 126.6, 126.5, 121.7, 120.7, 119.9, 110.2, 102.7, 44.1, 32.3, 20.1, 13.8; HRMS calc'd for $C_{22}H_{22}N$ $(M+H)^+$: 300.1747. found 300.1749.

Compound 1daf:

To a stirred solution of KOH (2.24 g, 40 mmol) in DMSO (20 mL was added 2-(2-naphthyl)indole (1aaf) (2.43 g, 10 mmol), and the mixture was stirred for 45 min. Then, sec-butyl bromide (2.7 g, 20 mmol) was added and the stirring was continued for additional 60 min. The mixture was diluted with water (20 mL) and extracted with benzene (3×50 mL). Combined organic layers were washed with water (3×100 mL), dried with $CaCl_2$ and concentrated in vacuum to obtain the titled compound as colorless solid. Yield 2.52 g (8.4 mmol, 84%); m.p.=103-104° C. (petroleum ether); $^1$H NMR (400 MHz, $CDCl_3$) δ, ppm: 7.99-7.91 (m, 4H), 7.69, (d, J=7.9 Hz, 1H), 7.63 (dd, J=8.4, 1.5 Hz, 1H), 7.59-7.55 (m, 3H), 7.44 (d, J=8.2 Hz, 1H), 7.27 (ddd, J=7.6, 7.5, 0.7 Hz, 1H) 7.18 (t, J=7.3 Hz, 1H), 6.66 (s, 1H), 4.15-4.13 (m, 2H), 2.15-2.04 (m, 1H), 0.69-067 (m, 6H); $^{13}$C NMR (100 MHz, $CDCl_3$) δ: 141.8, 138.0, 133.4, 132.9, 131.22, 128.7, 128.4, 128.3, 128.2, 127.9, 127.6, 126.6, 126.5, 121.6, 120.7, 119.9, 110.7, 103.0, 51.5, 29.1, 22.9, 20.2; HRMS calc'd for $C_{22}H_{22}N$ $(M+H)^+$: 300.1747. found 300.1750.

Compound 1eaf:

To a stirred solution of KOH (2.24 g, 40 mmol) in DMSO (20 mL was added 2-(2-naphthyl)indole (1aaf) (2.43 g, 10 mmol), and the mixture was stirred for 45 min. Then, benzyl bromide (3.4 g, 20 mmol) was added and the stirring was continued for an additional 45 min. The mixture was diluted with water (20 mL) and extracted with benzene (3×50 mL). Combined organic layers were washed with water (3×100 mL), dried with $CaCl_2$ and concentrated in vacuum to obtain the titled compound as colorless solid. Yield 3.07 g (9.2 mmol, 92%); m.p.=144-146° C. (toluene); $^1$H NMR (400 MHz, $CDCl_3$) δ, ppm: 7.89-7.84 (m, 3H), 7.76-7.70 (m, 2H), 7.57 (dd, J=8.5, 1.7 Hz, 1H), 7.51-7.49 (m, 2H), 7.32-7.24 (m, 4H), 7.20-7.17 (m, 2H), 7.08 (d, J=6.8 Hz, 2H), 6.77 (s, 1H), 5.43 (s, 2H); $^{13}$C NMR (100 MHz, $CDCl_3$) δ: 142.0, 138.4 (2C), 133.3, 133.0, 130.2, 128.9 (2C), 128.5, 128.4, 128.3 (2C), 127.8, 127.4, 127.2, 126.6, 126.5, 126.2 (2C), 122.2, 120.7, 120.4, 110.7, 102.9, 48.1; HRMS calc'd for $C_{25}H_{20}N$ $(M+H)^+$: 334.1590. found 334.1595.

Preparation of
2-aryl-2-(3-indolyl)acetohydroxamates 3. General
Method A

A mixture of a selected indole 1 (1 mmol) and a selected nitrostyrene 2 (1.2 mmol) in 80% PPA (3-4 g) was stirred at 65-70° C. for 1 h. The disappearance of the starting indole was monitored by TLC. After the indole had reacted completely, the mixture was cooled to rt, poured in water (50 mL) and treated with saturated $NH_4OH$ to pH 8. The formed precipitate was filtered and recrystallized from the indicated solvent.

Preparation of
2-aryl-2-(3-indolyl)acetohydroxamates 3. General
Method B

A mixture of a selected arylhydrazine 4 (1 mmol) and a selected methylaryl ketone 5 (1 mmol) in 80% PPA (2-3 g) was stirred at 100-110° C. for 40 min. The disappearance of the starting arylhydrazine was monitored by TLC. After the arylhydrazine had reacted completely, the temperature was decreased to 65-70° C. and a selected nitrostyrene 2 (1.2 mmol) was added. The mixture was stirred at this temperature for 1 h and the disappearance of the intermediate indole 1 was monitored by TLC. After the indole had reacted completely, the mixture was cooled to room temperature, poured in water (50 mL) and treated with saturated $NH_4OH$ to pH 8. The formed precipitate was filtered and recrystallized from the indicated solvent.

Compound 3aaaa.

Synthesized according to the general method A from 2-phenylindole (3aaa) and (2-nitrovinyl)benzene (2a) in 82% yield; Alternatively prepared according to the general method B starting from phenylhydrazine (4aa), acetophenone (5a) and (2-nitrovinyl)benzene (2a): 76%; m.p.=220-221° C. (toluene/petroleum ether); $^1$H NMR (500 MHz, $CDCl_3$) δ, ppm: 11.30 (br. s, 1H), 10.75 (br. s, 1H), 8.81 (br. s, 1H), 7.73 (d, J=8.0 Hz, 1H), 7.54-7.48 (m, 4H), 7.41 (dd, J=7.2, 7.1 Hz, 1H), 7.35 (d, J=8.1 Hz, 1H), 7.27-7.16 (m, 5H), 7.06 (dd, J=7.6, 7.4 Hz, 1H), 6.88 (t, J=7.4 Hz, 1H), 5.10 (s, 1H); $^{13}$C NMR (125 MHz, $CDCl_3$) δ, ppm: 168.6, 140.7, 136.2, 132.5, 128.6 (2C), 128.5 (2C), 128.0 (2C), 127.9 (2C), 127.7, 127.6, 126.1, 122.3, 121.1, 118.5, 110.9, 109.2, 46.0; EA: Calcd for $C_{22}H_{18}N_2O_2$: C, 77.17; H, 5.30; N, 8.18. Found: C, 77.33; H, 5.22; N, 8.11. HRMS calc'd for $C_{22}H_{18}N_2O_2Na$ $(M+Na)^+$: 365.1260. found 365.1272.

Compound 3aaab.

According to the method A, starting from 2-phenyl-1H-indole (3aaa) and 1-nitro-4-(2-nitrovinyl)benzene (2b): 73%; According to the method B, starting from phenylhydrazine (4aa), acetophenone (5a) and 1-nitro-4-(2-nitrovinyl)benzene (2b): 68%; m.p.=156-157° C. (toluene); $^1$H NMR (400 MHz, DMSO) δ, ppm: 11.44 (br. s, 1H), 10.89 (br. s, 1H), 8.96 (br. s, 1H), 8.14 (d, J=8.8 Hz, 2H), 7.65 (d, J=8.0 Hz, 1H), 7.49-7.46 (m, 4H), 7.42-7.36 (m, 5H), 7.09 (t, J=7.2 Hz, 1H), 6.92 (t, J=7.5 Hz, 1H), 5.20 (s, 1H); $^{13}$C NMR (100 MHz, DMSO) δ: 167.8, 148.6, 146.0, 136.7, 136.2, 132.2, 129.3 (2C), 128.7 (4C), 127.9, 127.4, 123.3 (2C), 121.6, 121.4, 118.9, 111.2, 108.0, 46.1; HRMS calc'd for $C_{22}H_{17}N_3O_4Na$ $(M+Na)^+$: 410.1111. found 410.1111.

Compound 3aaba.

According to the method A, starting from 2-(2-nitrophenyl)-1H-indole (3aab) and (2-nitrovinyl)benzene (2a): 68%; According to the method B, starting from phenylhydrazine (4aa), 2-nitroacetophenone (5b) and (2-nitrovinyl)benzene (2a): 61%; m.p.=118-119° C. (toluene); $^1$H NMR (400 MHz, DMSO) δ, ppm: 11.27 (br. s, 1H), 10.71 (br. s, 1H), 8.87 (br. s, 1H), 8.12 (dd, J=8.1, 0.9 Hz, 1H), 7.80-7.61 (m, 4H), 7.54 (d, J=7.4 Hz, 2H), 7.29 (d, J=8.0 Hz, 1H), 7.18-7.06 (m, 5H), 6.91 (t, J=7.4 Hz, 1H), 4.77 (s, 1H); $^{13}$C NMR (100 MHz, DMSO) δ: 166.4, 147.6, 139.9, 136.2, 134.2, 133.7, 133.1, 129.8, 127.8 (2C), 127.7 (3C), 127.0 (2C), 126.1, 124.5, 121.4, 118.5, 111.2, 110.9, 45.9; HRMS calc'd for $C_{22}H_{17}N_3O_4Na$ $(M+Na)^+$: 410.1111. found 410.1109.

Compound 3aaca.

According to the method A, starting from 2-(4-methoxyphenyl)-1H-indole (3aac) and (2-nitrovinyl)benzene (2a): 43%; According to the method B, starting from phenylhydrazine (4aa), 4-methoxyacetophenone (5c) and (2-nitrovinyl)benzene (2a): 35%; m.p.=133-134° C. (toluene); $^1$H NMR (400 MHz, DMSO) δ, ppm: 11.22 (br. s, 1H), 10.73 (br. s, 1H), 8.81 (br. s, 1H), 7.70 (d, J=8.0 Hz, 1H), 7.43 (d, J=8.5 Hz, 2H), 7.32 (d, J=8.0 Hz, 1H), 7.27-7.17 (m, 5H), 7.06-7.01 (m, 3H), 7.86 (t, J=7.5 Hz, 1H), 5.04 (s, 1H), 3.81 (s, 3H); $^{13}$C NMR (100 MHz, DMSO) δ: 169.1, 159.4, 141.3, 136.7, 136.5, 130.4 (2C), 128.5 (2C), 128.4 (2C), 128.3, 126.6, 125.4, 122.6, 121.3, 118.9, 114.6 (2C), 111.2, 109.0, 55.7, 46.6; HRMS calc'd for $C_{23}H_{20}N_2O_3Na$ $(M+Na)^+$: 395.1373. found 395.1366.

Compound 3aada.

According to the method A, starting from 2-methyl-1H-indole (3aad) and (2-nitrovinyl)benzene (2a): 46%; According to the method B, starting from phenylhydrazine (4aa), acetone (5d) and (2-nitrovinyl)benzene (2a): 27%; m.p.=110-112° C. (toluene); $^1$H NMR (400 MHz, DMSO) δ, ppm: 10.86 (br. s, 1H), 10.79 (br. s, 1H), 8.86 (br. s, 1H), 7.52 (d, J=7.9 Hz, 1H), 7.37 (s, 1H), 7.26-7.20 (m, 5H), 6.94 (ddd, J=7.4, 7.4, 0.6 Hz, 1H), 6.83 (t, J=7.2 Hz, 1H), 4.93 (s, 1H), 2.30 (s, 3H); $^{13}$C NMR (100 MHz, DMSO) δ: 168.7, 140.5, 135.1, 133.2, 128.1 (2C), 127.9 (2C), 127.7, 126.1, 119.9, 119.8, 118.0, 110.2, 108.5, 45.3, 11.9; HRMS calc'd for $C_{22}H_{17}N_3O_4Na$ (M+Na)$^+$: 303.1104. found 303.1103.

Compound 3aaea.

According to the method A, starting from 2-(1-naphthyl)-1H-indole (3aae) and (2-nitrovinyl)benzene (2a): 76%; According to the method B, starting from phenylhydrazine (4aa), 1-acetylnaphthalene (5e) and (2-nitrovinyl)benzene (2a): 70%; m.p.=110-112° C. (toluene); $^1$H NMR (400 MHz, DMSO, 338K) δ, ppm: 11.28 (br. s, 1H), 10.41 (br. s, 1H), 8.63 (br. s, 1H), 8.03-7.99 (m, 2H), 7.79-7.50 (m, 5H), 7.40-7.33 (m, 2H), 7.26-7.07 (m, 6H), 6.93 (t, J=7.4 Hz, 1H), 4.73 (s, 1H); $^{13}$C NMR (100 MHz, DMSO) δ: 168.8, 140.3, 136.3, 134.9, 133.2, 132.5, 130.0, 129.2, 128.6, 128.5, 128.1, 127.9 (2C), 127.2, 126.4, 126.0 (2C), 125.7, 125.5, 125.2, 122.4, 121.1, 118.4, 111.4, 110.8, 46.2; HRMS calc'd for $C_{26}H_{20}N_2O_2Na$ (M+Na)$^+$: 415.1417. found 415.1417.

Compound 3aafa.

According to the method A, starting from 2-(2-naphthyl)-1H-indole (3aaf) and (2-nitrovinyl)benzene (2a): 85%; According to the method B, starting from phenylhydrazine (4aa), 2-acetylnaphthalene (5f) and (2-nitrovinyl)benzene (2a): 73%; m.p.=152-154° C. (toluene). $^1$H NMR (500 MHz, DMSO) δ, ppm: 11.31 (br. s, 1H), 10.76 (br. s, 1H), 8.82 (br. s, 1H), 8.03-7.97 (m, 3H), 7.91 (dd, J=8.8, 2.1 Hz, 1H), 7.77 (d, J=8.1 Hz, 1H), 7.68 (dd, J=8.5, J=1.3 Hz, 1H), 7.58-7.56 (m, 2H), 7.38 (d, J=8.1 Hz, 1H), 7.29-7.17 (m, 5H), 7.09 (dd, J=7.8, 7.4 Hz, 1H), 6.91 (dd, J=7.8, 7.5 Hz, 1H), 5.19 (s, 1H); $^{13}$C NMR (125 MHz, DMSO) δ: 168.5, 140.8, 136.4, 135.9, 132.8, 132.2, 130.0, 128.1, 128.0 (2C), 127.9, 127.8, 127.6, 127.5, 127.4 126.6, 126.4, 126.3, 126.2, 122.3, 121.3, 118.6, 110.9, 109.9, 99.9, 45.8; EA: Calcd for $C_{26}H_{20}N_2O_2$: C, 79.57; H, 5.14; N, 7.14. Found: C, 79.68; H, 5.09; N, 7.16. HRMS calc'd for $C_{26}H_{20}N_2O_2Na$ (M+Na)$^+$: 415.1417. found 415.1419.

Compound 3abfa.

According to the method A, starting from 5-methyl-2-(2-naphthyl)-1H-indole (3abf) and (2-nitrovinyl)benzene (2a): 79%; According to the method B, starting from 4-tolylhydrazine (4ab), 2-acetylnaphthalene (5f) and (2-nitrovinyl)benzene (2a): 73%; m.p.=133-135° C. (toluene); $^1$H NMR (400 MHz, DMSO) δ, ppm: 11.34 (br. s, 1H), 10.75 (br. s, 1H), 8.82 (br. s, 1H), 8.00-7.87 (m, 5H), 7.65 (dd, J=8.65, 1.08 Hz, 1H), 7.60 (s, 1H), 7.57-7.54 (m, 2H), 7.29-7.17 (m, 6H), 7.92 (dd, J=8.2, 0.9 Hz, 1H), 5.17 (s, 1H), 2.31 (s, 3H); $^{13}$C NMR (100 MHz, DMSO) δ: 169.1, 141.4, 136.7, 135.3 (2C), 133.3, 132.7, 130.6, 128.6 (4C), 128.5, 128.4, 128.1, 127.9, 127.3, 127.1, 127.0, 126.8, 126.7, 123.5, 122.2, 111.2, 109.8, 46.7, 22.0; HRMS calc'd for $C_{27}H_{22}N_2O_2Na$ (M+Na)$^+$: 429.1573. found 439.1577.

Compound 3acfa.

According to the method B, starting from (4-methoxyphenyl)hydrazine (4ac), 2-acetylnaphthalene (5e) and (2-nitrovinyl)benzene (2a): 28%; m.p.=128-130° C. (toluene); $^1$H NMR (400 MHz, DMSO) δ, ppm: 11.31 (br. s, 1H), 10.80 (br. s, 1H), 8.85 (br. s, 1H), 8.01-7.88 (m, 4H), 7.65 (d, J=8.59 Hz, 1H), 7.59-7.53 (m, 2H), 7.37 (s, 1H), 7.30-7.17 (m, 5H), 7.75 (dd, J=8.7, 2.4 Hz, 1H), 5.16 (s, 1H), 3.64 (s, 3H); $^{13}$C NMR (100 MHz, DMSO) δ: 168.6, 152.8, 140.8, 136.8, 132.8, 132.2, 131.7, 130.1, 128.4, 128.3, 128.1 (4C), 128.0, 127.6, 127.3, 126.6, 126.5, 126.3, 126.2, 111.5, 111.2, 109.6, 104.5, 55.2, 46.3; HRMS calc'd for $C_{27}H_{22}N_2O_3Na$ (M+Na)$^+$: 445.1523. found 445.1523

Compound 3bafc.

According to the method A, starting from N-methyl-2-(2-naphthyl)-1H-indole (3baf) and 3-fluoro(2-nitrovinyl)benzene (2c): 54%; m.p.=133-134° C. (toluene/petroleum ether); $^1$H NMR (400 MHz, DMSO) δ, ppm: 10.69 (br. s, 1H), 8.89 (br. s, 1H), 8.07-7.92 (m, 4H), 7.73 (d, J=8.0 Hz, 1H), 7.61 (m, 2H), 7.50 (d, J=8.2 Hz, 2H), 7.26-7.17 (m, 4H), 7.08 (d, J=7.3 Hz, 1H), 7.0 (t, J=7.3 Hz, 1H), 4.84 (s, 1H), 3.59 (s. 3H); $^{13}$C NMR (100 MHz, DMSO) δ: 167.7, 159.8 (d, $^1J_{CF}$=247.2 Hz), 138.8, 136.9, 132.6, 132.5, 130.2, 129.9, 128.4 (d, $^3J_{CF}$=6.9 Hz), 128.2, 128.1, 127.9, 127.8, 127.6, 127.5, 126.7, 126.6, 126.5, 123.8, 121.4, 120.9, 119.2, 114.7 (d, $^2J_{CF}$=22.3 Hz), 109.8, 108.9, 40.4, 30.9; HRMS calc'd for $C_{27}H_{21}FN_2O_2Na$ (M+Na)$^+$: 447.1479. found 447.1493.

Compound 3bafa.

According to the method A, starting from N-methyl-2-(2-naphthyl)-1H-indole (3baf) and (2-nitrovinyl)benzene (2a): 75%; m.p.=114-115° C. (toluene/petroleum ether); $^1$H NMR (400 MHz, DMSO) δ, ppm: 10.66 (br. s, 1H), 8.84 (br. s, 1H), 8.03-7.91 (m, 4H), 7.77 (d, J=8.1 Hz, 1H), 7.62-7.60 (m, 2H), 7.52 (d, J=8.8 Hz, 1H), 7.48 (d, J=8.1 Hz, 1H), 7.26-7.14 (m, 7H), 6.98 (dd, J=7.8, 7.5 Hz, 1H), 4.85 (s, 1H), 3.60 (s, 3H); $^{13}$C NMR (100 MHz, DMSO) δ: 168.5, 140.7, 138.8, 137.1, 132.6, 132.5, 130.0, 128.4, 128.2, 128.1, 127.9 (4C), 127.6, 126.7, 126.5 (2C), 126.1, 122.3, 121.3, 118.8, 110.8, 109.5, 99.5, 46.4, 30.8; EA: Calcd for $C_{27}H_{22}N_2O_2$: C, 79.78; H, 5.46; N, 6.89. Found: C, 80.03; H, 5.39; N, 6.81. HRMS calc'd for $C_{27}H_{22}N_2O_2Na$ (M+Na)$^+$: 429.2416. found 429.2418.

Compound 3bafd.

According to the method A, starting from N-methyl-2-(2-naphthyl)-1H-indole (3baf) and 2-bromo(2-nitrovinyl)benzene (2d): 36%; m.p.=109-113° C. (toluene/petroleum ether); $^1$H NMR (400 MHz, CDCl$_3$) δ, ppm: 7.91 (d, J=8.2 Hz, 2H), 7.80 (d, J=7.00 Hz, 1H), 7.69-7.64 (m, 1H), 7.59-7.49 (m, 5H), 7.42 (d, J=8.2 Hz, 1H), 7.30 (d, J=8.2 Hz, 1H), 7.30 (d, J=7.6 Hz, 1H), 7.17-7.13 (m, 2H), 7.09-7.06 (m, 1H), 5.43 (s, 1H), 3.68 (s, 3H); $^{13}$C NMR (100 MHz, DMSO) δ, ppm: 167.6, 139.8, 139.0, 137.0, 132.5, 132.4, 132.3, 130.9, 129.8, 128.4, 128.2, 128.1, 127.8, 127.6, 127.5, 127.2, 126.8, 126.6, 126.4, 123.9, 121.4, 120.2, 119.4, 110.0, 109.5, 47.1, 31.0; HRMS calc'd for $C_{27}H_{21}BrN_2O_2Na$(M+Na)$^+$: 507.0679. found 507.0677.

Compound 3aafe.

According to the method A, starting from 2-(2-naphthyl)-1H-indole (3aaf) and 4-isopropyl(2-nitrovinyl)benzene (2a): 73%; According to the method B, starting from phenylhydrazine (4aa), 2-acetylnaphthalene (5f) and 4-isopropyl(2-nitrovinyl)benzene (2e): 61%; m.p.=147-148° C. (toluene/petroleum ether). $^1$H NMR (400 MHz, DMSO) δ, ppm: 11.44 (br. s, 1H), 10.76 (br. s, 1H), 8.82 (br. s, 1H), 8.02-7.9 (m, 4H), 7.82 (d, J=8.1 Hz, 1H), 7.66 (dd, J=8.5, 1.59 Hz, 1H) 7.60-7.53 (m, 2H), 7.38 (d, J=8.1 Hz, 1H), 7.17-7.06 (m, 5H), 6.92 (ddd, J=15.0, 7.5, 0.5 Hz, 1H), 5.16 (s, 1H), 2.86-2.76 (m, 1H), 1.14 (d, J=6.9 Hz, 6H); $^{13}$C NMR (100 MHz, DMSO) δ, ppm: 168.8, 146.2, 138.1, 136.4, 136.0, 132.8, 132.2, 130.1, 128.1, 128.0 (2C), 127.9, 127.6, 127.5, 126.7, 126.5, 126.3, 125.9 (2C), 122.4, 121.3, 118.6, 111.0, 110.0, 45.9, 39.9, 33.0, 23.9 (2C); Calc'd for $C_{29}H_{26}N_2O_2$: C, 80.16; H, 6.03; N, 6.45. Found: C, 80.31; H, 5.95; N, 6.36. HRMS calc'd for $C_{29}H_{26}N_2O_2Na$ (M+Na)$^+$: 457.1884. found 457.1887.

Compound 3aaff.

According to the method A, starting from 2-(2-naphthyl)-1H-indole (3aaf) and 3,4-dimethoxy(2-nitrovinyl)benzene (2f): 60%; According to the method B, starting from phenylhydrazine (4aa), 2-acetylnaphthalene (5f) and 3,4-dimethoxy(2-nitrovinyl)benzene (2f): 56%; m.p.=143-144° C. (toluene); $^1$H NMR (400 MHz, DMSO) δ, ppm: 11.44 (br. s, 1H), 10.70 (br. s, 1H), 8.81 (br. s, 1H), 8.02-7.89 (m, 4H), 7.85 (d, J=8.1 Hz, 1H), 7.67 (dd, J=8.5, 1.4 Hz, 1H), 7.59-7.54 (m, 2H), 7.38 (d, J=8.0 Hz, 1H), 7.09 (t, J=7.2 Hz, 1H), 6.94 (t, J=7.3 Hz, 1H), 6.85-6.83 (m, 2H), 7.76 (dd, J=8.4, 1.5 Hz, 1H), 5.12 (s, 1H), 3.68 (s, 3H), 3.59 (s, 3H); $^{13}$C NMR (100 MHz, DMSO) δ: 168.8, 148.3, 147.4, 136.4, 136.0, 133.1, 132.8, 132.2, 130.1, 128.1, 127.9, 127.8, 127.6, 127.5, 126.7, 126.5, 126.3, 122.2, 121.3, 120.4, 118.6, 112.4, 111.6, 111.0, 110.2, 55.5, 54.4, 45.9; HRMS calc'd for $C_{28}H_{24}N_2O_4Na$ (M+Na)$^+$: 475.1628. found 475.1635

Compound 3aafg.

According to the method A, starting from 2-(2-naphthyl)-1H-indole (3aaf) and 4-fluoro(2-nitrovinyl)benzene (2g): 76%; According to the method B, starting from phenylhydrazine (4aa), 2-acetylnaphthalene (5f) and 4-fluoro(2-nitrovinyl)benzene (2g): 64%; m.p.=138-139° C. (toluene/petroleum ether). $^1$H NMR (400 MHz, DMSO) δ, ppm: 11.50 (br. s, 1H), 10.80 (br. s, 1H), 8.88 (br. s, 1H), 8.04-7.97 (m, 4H), 7.92 (dd, J=8.8, 2.1 Hz, 1H), 7.76 (d, J=8.1 Hz, 1H), 7.67 (dd, J=8.5, J=1.3 Hz, 1H), 7.59-7.55 (m, 2H), 7.39 (d, J=8.1 Hz, 1H), 7.27-7.23 (m, 2H), 7.13-7.08 (m, 3H), 6.93 (dd, J=7.8, 7.5 Hz, 1H), 5.18 (s, 1H); $^{13}$C NMR (100 MHz, DMSO) δ: 168.4, 160.7 (d, $^1J_{CF}$=242.5 Hz), 136.9 (d, $^4J_{CF}$=3.0 Hz), 136.4, 136.2, 132.8, 132.2, 130.0, 129.8 (d, $^3J_{CF}$=8.1 Hz, 2C), 128.1, 128.0, 127.7, 127.6, 127.5, 126.6, 126.5, 126.4, 122.0, 121.4, 118.8, 114.8 (d, $^2J_{CF}$=21.6 Hz, 2C), 111.0, 109.7, 45.5; EA: Calcd for $C_{26}H_{19}FN_2O_2$: C, 76.08; H, 4.67; N, 6.83. Found: C, 76.23; H, 4.62; N, 6.76. HRMS calc'd for $C_{26}H_{19}FN_2O_2Na$ (M+Na)$^+$: 432.1244. found 432.2432.

Compound 3aafh.

According to the method A, starting from 2-(2-naphthyl)-1H-indole (3aaf) and 2-chloro(2-nitrovinyl)benzene (2h): 84%; According to the method B, starting from phenylhydrazine (4aa), 2-acetylnaphthalene (5f) and 2-chloro(2-nitrovinyl)benzene (2h): 72%; m.p.=164-166° C. (toluene/petroleum ether). $^1$H NMR (500 MHz, DMSO) δ, ppm: 11.59 (br. s, 1H), 10.67 (br. s, 1H), 8.80 (br. s, 1H), 8.01-7.94 (m, 2H), 7.79 (d, J=8.6 Hz, 2H), 7.60-7.54 (m, 4H), 7.45 (t, J=8.2 Hz, 2H), 7.39 (dd, J=1.6, 5.5 Hz, 2H), 7.29-7.23 (m, 3H), 7.14 (t, J=7.3 Hz, 1H), 6.85 (t, J=7.6 Hz, 1H), 5.46 (s, 1H); $^{13}$C NMR (125 MHz, DMSO) δ: 167.5, 138.4, 136.3, 136.1, 133.0, 132.8, 132.2, 131.0, 129.9, 129.1, 128.4, 128.1, 128.0, 127.9, 127.6, 127.0, 126.6, 126.4, 126.2, 121.5, 120.8, 119.2, 111.3, 108.8, 99.5, 44.6; EA: Calcd for $C_{26}H_{19}ClN_2O_2$: C, 73.15; H, 4.49; N, 6.56. Found: C, 73.26; H, 4.42; N, 6.61. HRMS calc'd for $C_{26}H_{19}ClN_2O_2Na$ (M+Na)$^+$: 449.1027. found 449.1012.

Compound 3aafi.

According to the method A, starting from 2-(2-naphthyl)-1H-indole (3aaf) and 3,4-dichloro(2-nitrovinyl)benzene (2i): 45%; According to the method B, starting from phenylhydrazine (4aa), 2-acetylnaphthalene (5f) and 3,4-dichloro(2-nitrovinyl)benzene (2i): 43%; m.p.=144-150° C. (toluene/petroleum ether). $^1$H NMR (500 MHz, DMSO) δ, ppm: 11.58 (br. s, 1H), 10.85 (br. s, 1H), 8.97 (br. s, 1H), 8.01 (s, 1H), 7.98-7.91 (m, 2H), 7.73 (d, J=8.1 Hz, 1H), 7.65 (d, J=8.3 Hz, 2H), 7.58-7.52 (m, 3H), 7.43-7.36 (m, 2H), 7.18-7.11 (m, 2H), 6.97 (t, J=7.4 Hz, 1H), 5.21 (s, 1H); $^{13}$C NMR (125 MHz, DMSO) δ: 167.8, 141.8, 136.6, 136.4, 132.8, 132.3, 130.7, 130.4, 129.9, 129.7, 129.0, 128.6, 128.3, 128.1, 127.7, 127.6, 127.5, 126.6 (2C), 126.5, 121.6, 121.6, 119.1, 111.3, 108.6, 45.5; EA: Calcd for $C_{26}H_{18}Cl_2N_2O_2$: C, 67.69; H, 3.93; N, 6.07. Found: C, 67.83; H, 3.87; N, 6.15. HRMS calc'd for $C_{26}H_{18}Cl_2N_2O_2Na$ (M+Na)$^+$: 483.0638. found 483.0643, 485.0662.

Compound 3aafc.

According to the method A, starting from 2-(2-naphthyl)-1H-indole (3aaf) and 3-fluoro(2-nitrovinyl)benzene (2c): 75%; According to the method B, starting from phenylhydrazine (4aa), 2-acetylnaphthalene (5f) and 3-fluoro(2-nitrovinyl)benzene (2c): 64%; m.p.=126-127° C. (toluene/petroleum ether). $^1$H NMR (400 MHz, DMSO) δ, ppm: 11.54 (br. s, 1H), 10.86 (br. s., 1H), 8.92 (br. s., 1H), 8.03-7.90 (m, 4H), 7.74 (d, J=8.1 Hz, 1H), 7.65 (dd, J=8.4, 1.7 Hz, 1H), 7.60-7.54 (m, 2H), 7.41-7.28 (m, 2H), 7.25 (dd, J=5.1, 1.4 Hz, 2H), 7.16 (d, J=7.5 Hz, 1H), 7.11 (ddd, J=7.5, 7.5, 0.8 Hz, 1H), 6.95 (ddd, J=11.4, 7.6, 0.6 Hz, 1H), 5.19 (s., 1H); $^{13}$C NMR (100 MHz, DMSO) δ: 168.1, 162.0 ($^1J_{CF}$=242.0 Hz) 143.7 (d, $^3J_{CF}$=6.0 Hz), 136.4, 132.8, 132.3, 130.0, 129.9, 129.8, 128.0 (2C), 127.7, 127.6 (2C), 126.6, 126.5, 126.4, 124.2, 121.9, 121.4, 118.8, 114.7 (d, $^2J_{CF}$=21.8 Hz), 113.1 (d, $^2J_{CF}$=20.7 Hz), 111.1, 109.2, 46.0; HRMS calc'd for $C_{26}H_{19}FN_2O_2Na$ (M+Na)$^+$: 433.1323. found 433.1337.

Compound 3aafj.

According to the method A, starting from 2-(2-naphthyl)-1H-indole (3aaf) and 4-(trifluoromethoxy)(2-nitrovinyl)benzene (2j): 56%; According to the method B, starting from phenylhydrazine (4aa), 2-acetylnaphthalene (5f) and 4-(trifluoromethoxy)(2-nitrovinyl)benzene (2j): 52%; m.p.=136-137° C. (toluene/petroleum ether). $^1$H NMR (400 MHz, DMSO) δ, ppm: 11.52 (br. s., 1H), 10.83 (br. s., 1H), 8.9 (br. s., 1H), 8.02-7.90 (m, 4H), 7.75 (d, J=8.08 Hz, 1H), 7.65 (dd, J=9.2, 1.2 Hz, 1H), 7.59-7.54 (m, 2H), 7.40 (d, J=8.1 Hz, 1H), 7.33 (d, J=8.8 Hz, 2H), 7.26 (d, J=8.3 Hz, 2H), 7.10 (ddd, J=7.6, 7.5, 0.5 Hz, 1H), 6.94 (t, J=7.4 Hz, 1H), 5.22 (s, 1H); $^{13}$C NMR (100 MHz, DMSO) δ, ppm: 168.2, 146.7, 140.1, 136.4 (20), 136.3, 132.8, 132.2, 129.8 (2C), 128.0 (3C), 127.6 (2C), 126.6, 126.5, 126.4, 121.9, 121.4, 120.7 (2C), 120.0 (q, $^1J_{CF}$=255.5 Hz), 118.8, 111.1, 109.3, 45.6; HRMS calc'd for $C_{27}H_{19}F_3N_2O_2Na$ (M+Na)$^+$: 499.1240. found 499.1232

Compound 3aafk.

According to the method A, starting from 2-(2-naphthyl)-1H-indole (3aaf) and 3,4-dimethyl(2-nitrovinyl)benzene (2k): 70%; According to the method B, starting from phenylhydrazine (4aa), 2-acetylnaphthalene (5f) and 3,4-dimethyl(2-nitrovinyl)benzene (2k): 59%; m.p.=144-147° C. (toluene/petroleum ether). $^1$H NMR (400 MHz, DMSO) δ, ppm: 11.43 (br. s, 1H), 10.73 (br. s, 1H), 8.81 (br. s, 1H), 8.03-7.97 (m, 3H), 7.92-7.90 (m, 1H), 7.77 (d, J=8.2 Hz, 1H), 7.65 (dd, J=8.7, 1.6 Hz, 1H), 7.60-7.54 (m, 2H), 7.38 (d, J=8.0 Hz, 1H), 7.10-7.06 (m, 1H), 7.02-7.01 (m, 2H), 6.94-6.89 (m, 2H), 5.11 (s, 1H), 2.15 (s, 3H), 2.13 (s, 3H);); $^{13}$C NMR (100 MHz, DMSO) δ, ppm: 168.8, 138.1, 136.4, 136.0, 135.5, 133.9, 132.8, 132.2, 130.1, 129.1 (2C), 128.1, 128.0, 127.9, 127.6, 127.5, 126.7, 126.5, 126.3, 125.5, 122.4, 121.3, 118.5, 110.9, 110.1, 45.9, 19.6, 18.9; Calc'd for $C_{28}H_{24}N_2O_2$: C, 79.98; H, 5.75; N, 6.66. Found: C, 80.09; H, 5.69; N, 6.69. HRMS calc'd for $C_{28}H_{24}N_2O_2Na$ (M+Na)$^+$: 443.1730. found 443.1732.

Compound 3aafd.

According to the method A, starting from 2-(2-naphthyl)-1H-indole (3aaf) and 2-bromo(2-nitrovinyl)benzene (2d): 57%; According to the method B, starting from phenylhydrazine (4aa), 2-acetylnaphthalene (5f) and 2-bromo(2-nitrovinyl)benzene (2d): 55%; m.p.=134-135° C. (toluene/petroleum ether). $^1$H NMR (400 MHz, CDCl$_3$) δ, ppm: 8.45 (br. s, 1H), 7.88-7.86 (m, 3H), 7.71 (s, 1H), 7.59 (d, J=7.7 Hz, 2H), 7.55-7.50 (m, 3H), 7.45 (d, J=8.4 Hz, 1H), 7.41 (d, J=8.1 Hz, 1H), 7.22-7.17 (m, 2H), 7.13 (ddd, J=7.9, 7.6, 0.1 Hz, 1H), 7.08 (t, J=7.6 Hz, 1H), 5.65 (s, 1H); $^{13}$C NMR (100 MHz, CDCl$_3$) δ, ppm: 169.8, 137.7, 137.6, 136.3, 133.5, 133.4, 133.1, 131.1, 129.4, 129.1, 129.0, 128.5, 128.0, 127.9, 127.8, 127.7, 126.9, 126.8, 125.6, 125.3, 123.0, 121.1, 120.3, 111.4, 108.0, 48.1; HRMS calc'd for C$_{24}$H$_{21}$BrN$_2$O$_2$Na (M+Na)$^+$: 471.0679. found 471.0692.

Compound 3aafl.

According to the method A, starting from 2-(2-naphthyl)-1H-indole (3aaf) and 4-ethoxy(2-nitrovinyl)benzene (2l): 81%; According to the method B, starting from phenylhydrazine (4aa), 2-acetylnaphthalene (5f) and 4-ethoxy(2-nitrovinyl)benzene (2l): 72%; m.p.=157-161° C. (toluene/petroleum ether). $^1$H NMR (400 MHz, CDCl$_3$) δ, ppm: 8.36 (br. s, 1H), 8.35 (br. s, 1H), 7.86-7.77 (m, 4H), 7.55-7.49 (m, 4H), 7.39 (t, J=3.9 Hz, 1H), 7.22 (d, J=8.8 Hz, 2H), 7.16 (dd, J=7.4, 7.6 Hz, 1H), 7.04 (dd, J=7.5, 7.6 Hz, 1H), 6.81 (d, J=8.6 Hz, 2H), 5.29 (s, 1H), 3.99 (q, J=7.0 Hz, 2H), 1.40 (t, J=7.0 Hz, 3H); $^{13}$C NMR (125 MHz, CDCl$_3$) 5, ppm: 170.8, 158.3, 137.1, 136.3 (2C), 133.4, 133.0, 130.0 (2C) 129.4, 128.9, 128.3, 127.9 (2C) 127.6, 126.9, 126.8, 126.0, 122.9, 120.8, 120.7, 114.9 (2C), 111.3, 109.7, 63.6, 47.0, 15.0; EA: Calcd for C$_{28}$H$_{24}$N$_2$O$_3$: C, 77.04; H, 5.54; N, 6.42. Found: C, 77.23; H, 5.48; N, 6.32. HRMS calc'd for C$_{28}$H$_{24}$N$_2$O$_3$Na (M+Na)$^+$: 459.1679. found 459.1673.

Compound 3aafm.

According to the method A, starting from 2-(2-naphthyl)-1H-indole (3aaf) and 4-methyl(2-nitrovinyl)benzene (2m): 80%; According to the method B, starting from phenylhydrazine (4aa), 2-acetylnaphthalene (5f) and 4-methyl(2-nitrovinyl)benzene (2m): 72%; m.p.=135-140° C. (toluene/petroleum ether). $^1$H NMR (400 MHz, DMSO) δ, ppm: 11.46 (br. s, 1H), 10.79 (br. s, 1H), 8.85 (br. s, 1H), 8.03-7.90 (m, 4H), 7.76 (d, J=8.1 Hz, 1H), 7.67 (dd, J=8.6, 1.4 Hz, 1H), 7.59-7.54 (m, 2H), 7.39-7.36 (m, 2H), 7.29-7.17 (m, 3H), 7.08 (ddd, J=7.5, 7.5, 1.0 Hz, 1H), 6.9 (ddd, J=7.5, 7.5, 0.8 Hz, 1H), 5.19 (s, 1H), 2.44 (s, 3H); $^{13}$C NMR (100 MHz, DMSO) δ, ppm: 168.6, 140.8, 136.4, 136.1, 132.8, 132.2, 130.0 (2C), 128.1 (2C), 128.0 (3C), 127.9, 127.6, 127.5, 126.6, 126.5, 126.3, 126.2, 122.3, 121.3, 118.6, 111.0, 109.9, 46.2, 35.8; Calc'd for C$_{27}$H$_{22}$N$_2$O$_2$: C, 79.78; H, 5.46; N, 6.89. Found: C, 79.91; H, 5.40; N, 6.94. HRMS calc'd for C$_{27}$H$_{22}$N$_2$O$_2$Na (M+Na)$^+$: 429.1573. found 429.1703.

Compound 3aafn.

According to the method A, starting from 2-(2-naphthyl)-1H-indole (3aaf) and 3-methyl(2-nitrovinyl)benzene (2n): 76%; According to the method B, starting from phenylhydrazine (4aa), 2-acetylnaphthalene (5f) and 3-methyl(2-nitrovinyl)benzene (2n): 69%; m.p.=155-156° C. (toluene/petroleum ether). $^1$H NMR (400 MHz, DMSO) δ, ppm: 11.45 (br. s, 1H), 10.76 (br. s, 1H), 8.83 (br. s, 1H), 8.02-7.89 (m, 4H), 7.76 (d, J=8.6 Hz, 1H), 7.66 (dd, J=8.5, 2.5 Hz, 1H), 7.59-7.54 (m, 2H), 7.39-7.37 (m, 2H), 7.30-7.06 (m, 3H), 7.03-6.98 (m, 1H), 6.93-6.89 (m, 1H), 5.15 (s, 1H), 2.22 (s, 3H); $^{13}$C NMR (100 MHz, DMSO) δ, ppm: 168.6, 140.7, 137.0, 136.4, 136.1, 132.8, 132.2, 130.1, 128.6, 128.1, 128.0, 127.9, 127.8, 127.6, 127.5, 126.9, 126.7, 126.5, 126.4, 125.2, 122.3, 121.3, 118.6, 111.0, 109.9, 108.3, 46.2; Calc'd for C$_{27}$H$_{22}$N$_2$O$_2$: C, 79.78; H, 5.46; N, 6.89. Found: C, 79.91; H, 5.39; N, 6.96. HRMS calc'd for C$_{27}$H$_{22}$N$_2$O$_2$Na (M+Na)$^+$: 429.1573. found 429.1569.

Compound 3aafo.

According to the method A, starting from 2-(2-naphthyl)-1H-indole (3aaf) and 4-(N,N-diethylamino)(2-nitrovinyl)benzene (2o): 53%; According to the method B, starting from phenylhydrazine (4aa), 2-acetylnaphthalene (5f) and 4-(N,N-diethylamino)(2-nitrovinyl)benzene (2o): 50%; m.p.=168-170° C. (chloroform). $^1$H NMR (400 MHz, DMSO) δ, ppm: 11.40 (br. s, 1H), 10.65 (br. s, 1H), 8.76 (br. s, 1H), 8.01 (d, J=9.6 Hz, 2H), 7.98-7.90 (m, 2H), 7.85 (d, J=8.1 Hz, 1H), 7.67 (dd, J=8.5, 1.7 Hz, 1H), 7.59-7.53 (m, 2H), 7.36 (d, J=8.1 Hz, 1H), 7.07 (ddd, J=7.6, 7.1, 1.1 Hz, 1H), 7.02 (d, J=8.8 Hz, 2H), 6.91 (ddd, J=7.3, 7.1, 0.9 Hz, 1H), 6.55 (d, J=8.9 Hz, 2H), 5.05 (s, 1H), 3.26 (q, J=7.0 Hz, 4H), 1.03 (t, J=7.0 Hz, 6H); $^{13}$C NMR (100 MHz, DMSO) δ, ppm: 169.3, 145.9, 136.4, 135.7, 132.9, 132.2, 130.3, 128.9 (2C), 128.1, 128.0 (2C), 127.6, 127.5, 127.1, 126.7, 126.5, 126.3, 122.7, 121.3, 118.5, 111.3 (2C), 110.9, 110.8, 45.4, 43.6 (2C), 12.4 (2C); Calc'd for C$_{30}$H$_{29}$N$_3$O$_2$: C, 77.73; H, 6.31; N, 9.06. Found: C, 77.85; H, 6.27; N, 8.99. HRMS calc'd for C$_{30}$H$_{29}$N$_3$O$_2$Na (M+Na)$^+$: 486.2152. found 486.2159.

Compound 3aafp.

According to the method A, starting from 2-(2-naphthyl)-1H-indole (3aaf) and 4-(N,N-dimethylamino)(2-nitrovinyl)benzene (2p): 45%; According to the method B, starting from phenylhydrazine (4aa), 2-acetylnaphthalene (5f) and 4-(N,N-diethylamino)(2-nitrovinyl)benzene (2p): 43%; m.p.=168-167° C. (toluene/petroleum ether). $^1$H NMR (400 MHz, DMSO) δ, ppm: 11.40 (br. s, 1H), 10.67 (br. s, 1H), 7.77 (br. s, 1H), 8.03-7.90 (m, 4H), 7.80 (d, J=8.1 Hz, 1H), 7.67 (dd, J=8.6, 1.6 Hz, 1H), 7.60-7.53 (m, 2H), 7.36 (d, J=8.1 Hz, 1H), 7.09-7.04 (m, 3H), 6.9 (ddd, J=8.1, 7.1, 1.0 Hz, 1H), 6.63 (dt, J=8.9, 2.4 Hz, 2H), 5.07 (s, 1H), 2.82 (s, 6H); $^{13}$C NMR (100 MHz, DMSO) δ, ppm: 169.2, 149.0, 136.4, 135.8, 132.9, 132.2, 130.2, 128.6 (2C), 128.3, 128.2, 128.1, 128.0, 127.6, 127.4, 126.7, 126.5, 126.3, 122.7, 121.3, 118.5, 112.2 (2C), 110.9, 110.7, 45.4, 40.25 (2C); Calc'd for C$_{28}$H$_{25}$N$_3$O$_2$: C, 77.22; H, 5.79; N, 9.65. Found: C, 77.39; H, 5.71; N, 9.59. HRMS calc'd for C$_{28}$H$_{25}$N$_3$O$_2$Na (M+Na)$^+$: 458.1839. found 458.1846.

Compound 3cafa.

According to the method A, starting from N-butyl-2-(2-naphthyl)-1H-indole (3caf) and (2-nitrovinyl)benzene (2a): 83%; m.p.=110-112° C. (carbon tetrachloride). $^1$H NMR (400 MHz, DMSO) δ, ppm: 10.63 (br. s, 1H), 8.83 (br. s, 1H), 8.06-7.97 (m, 4H), 7.76 (d, J=8.0 Hz, 1H), 7.63-7.59 (m, 2H), 7.49 (d, J=8.2 Hz, 1H), 7.23-7.12 (m, 7H), 6.95 (t, J=7.5 Hz, 1H), 4.77 (s, 1H), 4.05 (m, 2H), 1.49 (m, 2H), 1.02 (q, J=7.37 Hz, 2H), 0.62 (t, J=7.29 Hz, 3H); $^{13}$C NMR (100 MHz, DMSO) δ, ppm: 168.5, 140.7, 138.6, 136.3, 132.7, 132.6, 128.7, 128.0, 127.9 (4C), 127.8 (2C), 127.7, 126.7 (2C), 126.5 (2C), 126.12, 122.5, 121.3, 118.8, 111.1, 109.0, 46.3, 43.0, 31.5, 19.2, 13.4. HRMS calc'd for C$_{30}$H$_{28}$N$_2$O$_2$Na (M+Na)$^+$: 471.2043. found 417.2054.

Compound 3dafa.

According to the method A, starting from N-(sec-butyl)-2-(2-naphthyl)-1H-indole (3daf) and (2-nitrovinyl)benzene (2a): 80%; m.p.=131-133° C. (carbon tetrachloride). $^1$H NMR (400 MHz, DMSO) 5, ppm: 10.64 (br. s, 1H), 8.83 (br. s, 1H), 8.09-7.88 (m, 4H), 7.54 (d, J=8.0 Hz, 1H), 7.62-7.56 (m, 2H), 7.51 (d, J=8.3 Hz, 1H), 7.53-7.11 (m, 7H), 6.94 (t, J=7.6 Hz, 1H), 4.77 (s, 1H), 3.99-3.90 (m, 2H), 1.88-1.87 (m, 1H), 0.56-0.54 (m, 6H); $^{13}$C NMR (100 MHz, CDCl$_3$) δ, ppm: 168.6, 140.7, 138.8, 136.7, 132.7, 132.5, 128.8, 128.0, 127.9 (4C), 127.8 (2C), 127.7, 126.7, 126.6, 126.5, 126.1, 122.4, 121.2 (2C), 118.7, 111.2, 110.3, 50.5, 46.3, 28.4, 19.8 (2C); HRMS calc'd for C$_{30}$H$_{28}$N$_2$O$_2$Na (M+Na)$^+$: 471.2043. found 417.2048.

Compound 3cafe.

According to the method A, starting from N-butyl-2-(2-naphthyl)-1H-indole (3caf) and 4-isopropyl(2-nitrovinyl)benzene (2e): 68%; m.p.=132-134° C. (carbon tetrachloride). $^1$H NMR (400 MHz, DMSO) δ, ppm: 10.60 (br. s, 1H), 8.05-7.94 (m, 4H), 7.81 (d, J=8.0 Hz, 1H), 7.62-7.58 (m, 2H), 7.48 (d, J=8.2 Hz, 2H), 7.14 (t, J=7.3 Hz, 1H), 7.08-7.02 (m, 4H), 6.96 (t, J=7.5 Hz, 1H), 4.74 (s, 1H), 4.04-4.03 (m, 2H), 2.82-2.74 (m, 1H), 1.52-1.45 (m, 2H), 1.12 (d, J=6.9 Hz, 6H), 1.02 (q, J=7.38 Hz, 2H), 0.62 (t, J=7.3 Hz, 3H); $^{13}$C NMR (100 MHz, DMSO) δ, ppm: 168.7, 146.0, 138.5, 138.0, 136.3, 132.7, 132.5, 130.0, 128.7, 128.3, 128.1, 128.0, 127.8 (2C), 127.7, 126.7 (2C), 126.5, 125.8 (2C), 122.5, 121.2, 118.7, 111.3, 109.8, 46.0, 43.0, 32.9, 31.5, 23.8 (2C), 19.2, 13.4; HRMS calc'd for $C_{33}H_{34}N_2O_2Na$ (M+Na)$^+$: 513.2512. found 513.2521.

Compound 3eafa.

According to the method A, starting from N-benzyl-2-(2-naphthyl)-1H-indole (3eaf) and (2-nitrovinyl)benzene (2a): 75%; m.p.=118-120° C. (carbon tetrachloride). $^1$H NMR (400 MHz, DMSO) δ, ppm: 10.68 (br.s, 1H), 8.86 (br. s, 1H), 7.99-7.87 (m, 4H), 7.77 (d, 1H), 7.43-7.34 (m, 3H), 7.26-7.15 (m, 8H), 7.08 (t, 1H), 6.95 (t, 1H), 6.85 (d, 1H), 5.32 (m, 2H), 4.83 (s, 1H); $^{13}$C NMR (100 MHz, DMSO) δ, ppm: 168.5, 140.6, 138.9, 138.2, 136.6, 132.6 (2C), 128.4 (2C), 128.0 (4C), 127.8 (2C), 127.7, 127.0, 126.9, 126.8, 126.6, 126.2, 126.0 (3C), 122.6, 121.6, 119.2, 111.7, 110.3, 46.8, 46.4; HRMS calc'd for $C_{33}H_{26}N_2O_2Na$ (M+Na)$^+$: 505.1883. found 505.1886.

Synthesis of compound 6.

A solution of 3aaaa (390 mg, 0.99 mmol) and PCl$_3$ (140 mg, 1.02 mmol) in EtOAc is refluxed for 2 h. After the reaction mixture is allowed to cool down to rt, it is washed with NaHCO$_3$ (15 mL) and water (2×15 mL). The solvent is then removed on the rotary evaporator and the residue is recrystallized from toluene to afford 266 mg (0.74 mmol, 75%) of nitrile 6. m.p.=146-147° C. (toluene); $^1$H NMR (400 MHz, DMSO) δ, ppm: 11.85 (br.s, 1H), 8.09-7.94 (m, 4H), 7.7 (dd, J=8.5, 1.8 Hz, 1H) 7.61-7.57 (m, 2H), 7.49 (d, J=8.1 Hz, 1H), 7.45 (d, J=8.0 Hz, 1H), 7.39-7.29 (m, 5H), 7.19 (ddd, J=8.1, 7.1, 1.07 Hz, 1H), 7.05 (ddd, J=8.0, 7.1, 0.9 Hz, 1H), 6.08 (s, 1H); $^{13}$C NMR (100 MHz, DMSO) δ, ppm: 136.6, 136.4, 136.3, 132.8, 132.5, 129.0 (2C), 128.8, 128.6, 128.2, 127.7, 127.5, 126.8 (5C), 126.4, 126.1, 122.3, 120.0, 119.8, 118.8, 111.9, 105.0, 32.7; HRMS calc'd for $C_{26}H_{18}N_2Na$ (M+Na)$^+$: 381.1362. found 381.1362.

Synthesis of compound 7.

A solution of nitrile 6 (360 mg, 1.00 mmol) was stirred in 80% PPA (3 g) for 1 h at 80° C. The reaction mixture was then allowed to cool down to rt, poured in water (15 mL) and neutralized with NH$_4$OH. The obtained precipitate was collected by filtration and recrystallized from EtOAc to yield 369 mg (0.98 mmol, 98%) of amide 7. m.p.=333-335° C. (EtOAc); $^1$H NMR (400 MHz, DMSO) δ, ppm: 11.49 (br. s., 1H), 8.03-7.87 (m, 4H), 7.69 (dd, J=8.6, 1.3 Hz, 1H), 7.62 (d, J=8.1 Hz, 1H), 7.63-7.59 (m, 2H), 7.41-7.36 (m, 2H), 7.29-7.16 (m, 5H), 7.09 (t, J=7.8 Hz, 1H), 6.91 (t, 7.3 Hz, 1H), 5.28 (s, 1H); $^{13}$C NMR (100 MHz, DMSO) δ, ppm: 173.6, 141.2, 136.5, 136.1, 132.8, 132.2, 130.1, 128.5 (2C), 128.1 (3C), 127.9, 127.7, 127.4 (3C), 126.6, 126.4, 126.2, 121.5, 121.4, 118.8, 111.2, 110.4, 49.1; HRMS calc'd for $C_{26}H_{20}N_2ONa$ (M+Na)$^+$: 399.1468. found 399.1478.

Cell Culture

Human cancer cell lines were obtained from the American Type Culture Collection (ATCC, Manassas, Va., USA), the European Collection of Cell Culture (ECACC, Salisbury, UK) and the Deutsche Sammlung von Mikroorganismen and Zellkulturen (DSMZ, Braunschweig, Germany). Human cervical adenocarcinoma HeLa cells were cultured in DMEM supplemented with 10% fetal bovine serum (FBS). Human mammary carcinoma MCF-7 cells were cultured in RPMI supplemented with 10% FBS. The U87 cells (ATCC HTB-14) were cultured in DMEM culture medium, while the A549 cells (DSMZ ACC107) were cultured in RPMI culture medium supplemented with 10% heat-inactivated FBS. The glioblastoma multiforme Hs683 (ATCC HTB-138) and the T98G (ATCC CRL-1690) cell lines were cultivated in DMEM supplemented with 10% FBS. The Human uterine sarcoma MES-SA and MES-SA/Dx5 cells were cultured in RPMI-1640 medium supplemented with 10% FBS with MES SA/Dx5 maintained in the presence of 500 nM Doxorubicin (Sigma). SKMEL-28 cells (ATCC HTB72) and U373 glioblastoma cells (ECACC 08061901) were cultured in RPMI culture medium supplemented with 10% heat-inactivated FBS. Cell culture media were supplemented with 4 mM glutamine (Lonza code BE17-605E), 100 μg/mL gentamicin (Lonza code 17-5182), and penicillin-streptomycin (200 units/ml and 200 μg/ml) (Lonza code 17-602E). Neurosphere culture GBM 031810 was established using known methods and maintained in Neurobasal medium (Invitrogen Carlsbad, Calif.) with B27 supplement (20 ul/ml; Invitrogen), Glutamax (10 ul/ml; Invitrogen), fibroblast growth factor-2 (20 ng/ml; Peprotech, Rocky Hill, N.J., USA), epidermal growth factor (20 ng/ml; Peprotech), heparin (32 IE/ml; Sigma Aldrich, St. Louis, Mo.), and penicillin-streptomycin (1×, Invitrogen). Growth factors and heparin were renewed twice weekly. All cell lines were cultured in T25 flasks, maintained and grown at 37° C., 95% humidity, 5% CO$_2$.

Antiproliferative Properties

Antiproliferative properties of the synthesized compounds were evaluated by the MTT assay. All compounds were dissolved in DMSO at a concentration of either 100 mM or 50 mM prior to cell treatment. The cells were trypsinized and seeded at 4×10$^3$ cells per well into 96-well plates. The cells were grown for 24 h, treated with compounds at concentrations ranging from 0.001 to 100 μM and incubated for 48 h in 200 μL media. 20 μL of MTT reagent in serum free medium (5 mg/mL) was added to each well and incubated further for 2 h. Media was removed and the resulting formazan crystals were re-solubilized in 200 μL of DMSO. A$_{490}$ was measured using a Molecular Devices Thermomax plate reader. The experiments were performed in quadruplicate and repeated at least twice for each compound per cell line. Cells treated with 0.1% DMSO were used as a negative control; 1 μM phenyl arsine oxide (PAO) was used as a positive control.

Selection of Doxorubicin Resistant Cells

Selection of the MES-SA/Dx5 cell line was done according to W. G. Harker and B. I. Sikic, Cancer Res. 1985, p. 45, 4091. The cells were split and allowed to adhere overnight. The next day cells were initially exposed to a DOX concentration of 100 nM, which represented the GI$_{50}$ concentration. The cells were maintained at this DOX concentration until their growth rate reached that of the untreated cells. The DOX concentration was then increased in two-fold increments following the same growth criteria at each concentration to a final DOX concentration of 500 nM. Each new DOX concentration required approximately 2 passages to reach the growth rate of the untreated cells.

Quantitative Videomicroscopy

The effects of 3aafa on the viability of human U373 glioblastoma and SKMEL melanoma cells were characterized in vitro using computer-assisted phase contrast video microscopy.

Redifferentiation of Malignant U87 Cells to an Astrocytic Phenotype.

U87 cells were plated at a density of $5\times10^4$ cells per well in 24-well plate in DMEM supplemented with 10% FBS. The following day, the cells in each well were re-fed with 1 mL of fresh DMEM/10% FBS, and treated with 3aafa to a final concentration between 15 and 5 μM. Cells were placed into the $CO_2$ incubator and media was not replaced for the duration of the experiment.

LogP Calculations

The log P values were determined theoretically using three different programs and the data was then used to find the mean log P and standard deviation. These programs included ChemAxon's Marvin sketch the Molinspiration software and VCCLAB's ALOGPS software.

The present invention is, of course, in no way restricted to the specific disclosure of the specification and drawings, but also encompasses any modifications within the scope of the appended claims.

The invention claimed is:

1. A pharmaceutical composition comprising a pharmaceutically acceptable excipient or carrier and a compound of Formula 3 as follows:

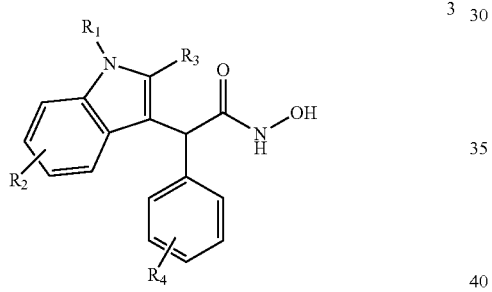

or a pharmaceutically acceptable salt or prodrug thereof, wherein:

$R_1$, $R_2$, and $R_3$ are optionally substituted and are hydrogen, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, acyloxyalkyl, hydroxyl, alkoxy, acetoxy, amino, alkylamino, acetamido and $R_4$ is optionally substituted and is hydrogen, halogen, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, acyloxyalkyl, hydroxyl, alkoxy, acetoxy, amino, alkylamino, acetamido.

2. A method of treating drug-resistant cancer in the form of uterine cancer, cervical cancer, breast cancer, brain cancer, liver cancer, bone cancer, lung cancers, neuroendocrine tumors, melanoma, leukemia and lymphoma, comprising administering an effective amount of one or more compounds of Formula 3 of claim 1.

3. A method of producing the compounds of Formula 3 of claim 1, comprising:

reacting indoles of formula 1,

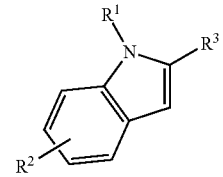

wherein $R_1$, $R_2$, and $R_3$ are optionally substituted and are hydrogen, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, acyloxyalkyl, hydroxyl, alkoxy, acetoxy, amino, alkylamino, acetamido, with beta-nitrostyrenes of formula 2,

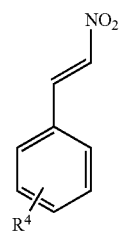

where $R_4$ is optionally substituted and is hydrogen, halogen, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, acyloxyalkyl, hydroxyl, alkoxy, acetoxy, amino, alkylamino, acetamido, in polyphosphoric acid at 70° C.

4. A method of producing the compounds of Formula 3 of claim 1, comprising:

reacting arylhydrazines of formula 4,

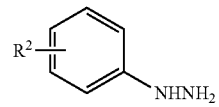

wherein $R_2$ is optionally substituted and is hydrogen, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, acyloxyalkyl, hydroxyl, alkoxy, acetoxy, amino, alkylamino, acetamido, with ketones of formula 5,

wherein $R_3$ is haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, acyloxyalkyl, at 100° C., followed by lowering the reaction temperature to 70° C. prior to the addition of beta-nitrostyrenes of formula 2,

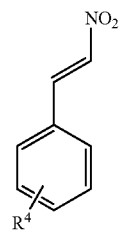

wherein $R_2$ is optionally substituted and is hydrogen, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, carbocycloalkyl, heterocycloalkyl, hydroxyalkyl, aminoalkyl, carboxyalkyl, nitroalkyl, cyanoalkyl, acetamidoalkyl, acyloxyalkyl, hydroxyl, alkoxy, acetoxy, amino, alkylamino, acetamido.

* * * * *

UNITED STATES PATENT AND TRADEMARK OFFICE
CERTIFICATE OF CORRECTION

| | | |
|---|---|---|
| PATENT NO. | : 9,206,124 B2 | Page 1 of 1 |
| APPLICATION NO. | : 14/516543 | |
| DATED | : December 8, 2015 | |
| INVENTOR(S) | : Alexander V. Aksenov et al. | |

It is certified that error appears in the above-identified patent and that said Letters Patent is hereby corrected as shown below:

Title Page, item (72) Inventors: First named inventor's name is misspelled - correct spelling should be Alexander V. Aksenov Signed and Sealed this
Twenty-sixth Day of April, 2016

Michelle K. Lee
*Director of the United States Patent and Trademark Office*